(12) United States Patent
Nonn et al.

(10) Patent No.: US 12,015,857 B2
(45) Date of Patent: Jun. 18, 2024

(54) LIGHT FIELD CAPTURE, COMPRESSION, TRANSMISSION AND RECONSTRUCTION

(71) Applicant: Proprio, Inc., Seattle, WA (US)

(72) Inventors: Thomas Ivan Nonn, Kenmore, WA (US); Tze-Yuan Cheng, Bellevue, WA (US); James Andrew Youngquist, Seattle, WA (US)

(73) Assignee: PROPRIO, INC., Seattle, WA (US)

( * ) Notice: Subject to any disclaimer, the term of this patent is extended or adjusted under 35 U.S.C. 154(b) by 0 days.

(21) Appl. No.: 17/836,979

(22) Filed: Jun. 9, 2022

(65) Prior Publication Data

US 2023/0403477 A1    Dec. 14, 2023

(51) Int. Cl.
H04N 25/13        (2023.01)
A61B 90/00        (2016.01)

(52) U.S. Cl.
CPC ............. *H04N 25/13* (2023.01); *A61B 90/37* (2016.02); *A61B 2090/372* (2016.02)

(58) Field of Classification Search
CPC ................ H04N 9/04551; A61B 90/37; A61B 2090/372
See application file for complete search history.

(56) References Cited

U.S. PATENT DOCUMENTS

| | | | |
|---|---|---|---|
| 10,949,986 B1 | 3/2021 | Colmenares et al. | |
| 11,295,460 B1 | 4/2022 | Aghdasi et al. | |
| 2011/0087237 A1 | 4/2011 | Viswanathan | |
| 2016/0300017 A1 | 10/2016 | Lee et al. | |
| 2017/0041296 A1 | 2/2017 | Ford et al. | |
| 2019/0139189 A1 | 5/2019 | Srinivasamurthy et al. | |
| 2019/0354693 A1 | 11/2019 | Yoon et al. | |
| 2020/0044863 A1 | 2/2020 | Yadlin et al. | |
| 2020/0105065 A1 | 4/2020 | Youngquist et al. | |
| 2020/0314362 A1* | 10/2020 | Roh | H04N 5/37457 |
| 2020/0334229 A1 | 10/2020 | Harrison et al. | |
| 2021/0044775 A1 | 2/2021 | Lee et al. | |
| 2021/0319895 A1 | 10/2021 | Joao | |

OTHER PUBLICATIONS

U.S. Appl. No. 16/457,780, titled "Synthesizing an Image From a Virtual Perspective Using Pixels From a Physical Imager Array Weighted Based on Depth Error Sensitivity," and filed Jun. 28, 2019.
International Search Report and Written Opinion from PCT Application No. PCT/US2023/067930 dated Oct. 5, 2023 (12 pages).
International Search Report and Written Opinion received in Application No. PCT/US23/67930, dated Oct. 5, 2023, 12 pages.

\* cited by examiner

*Primary Examiner* — Mark D Remaly
(74) *Attorney, Agent, or Firm* — Perkins Coie LLP

(57) ABSTRACT

Systems, devices, and methods for collection, editing, and playback of data collected from an imaging system for generating a virtual perspective of a scene are disclosed. In one example perspective, an imaging system includes a camera array configured to capture multiple images of a scene. Each of the multiple images includes color data represented in a Bayer pattern that includes a blue channel, two green channels, and a red channel. The system also includes an image processing device configured to receive the multiple images captured by the camera array, split each of the multiple images represented in the Bayer pattern into four individual color planes, form at least one set of data by combining the four individual color planes of the multiple images, and compress the at least one set of data.

16 Claims, 17 Drawing Sheets

|   |   |   |   |
|---|---|---|---|
| B | G | B | G |
| G | R | G | R |
| B | G | B | G |
| G | R | G | R |

*FIG. 4*

LIGHT FIELD CAPTURE, COMPRESSION, TRANSMISSION AND RECONSTRUCTION

TECHNICAL FIELD

The present technology generally relates to collection, editing, and playback of data, such as light field data, collected from a multicamera imaging system.

BACKGROUND

In a mediated reality system, an image processing system adds, subtracts, and/or modifies visual information representing an environment. The visual information can be captured using an array of multiple cameras. For surgical applications, a mediated reality system can enable a surgeon to view a surgical site from a desired perspective together with contextual information that assists the surgeon in more efficiently and precisely performing surgical tasks. In some implementations, to reconstruct an image of the environment, mediated reality systems can capture a large amount of data including (i) image data from multiple ones of the cameras positioned at different angles and orientations relative to the environment and (ii) depth information about the environment.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIG. 4 illustrates an example four-color Bayer pattern.

DETAILED DESCRIPTION

Figure 1:
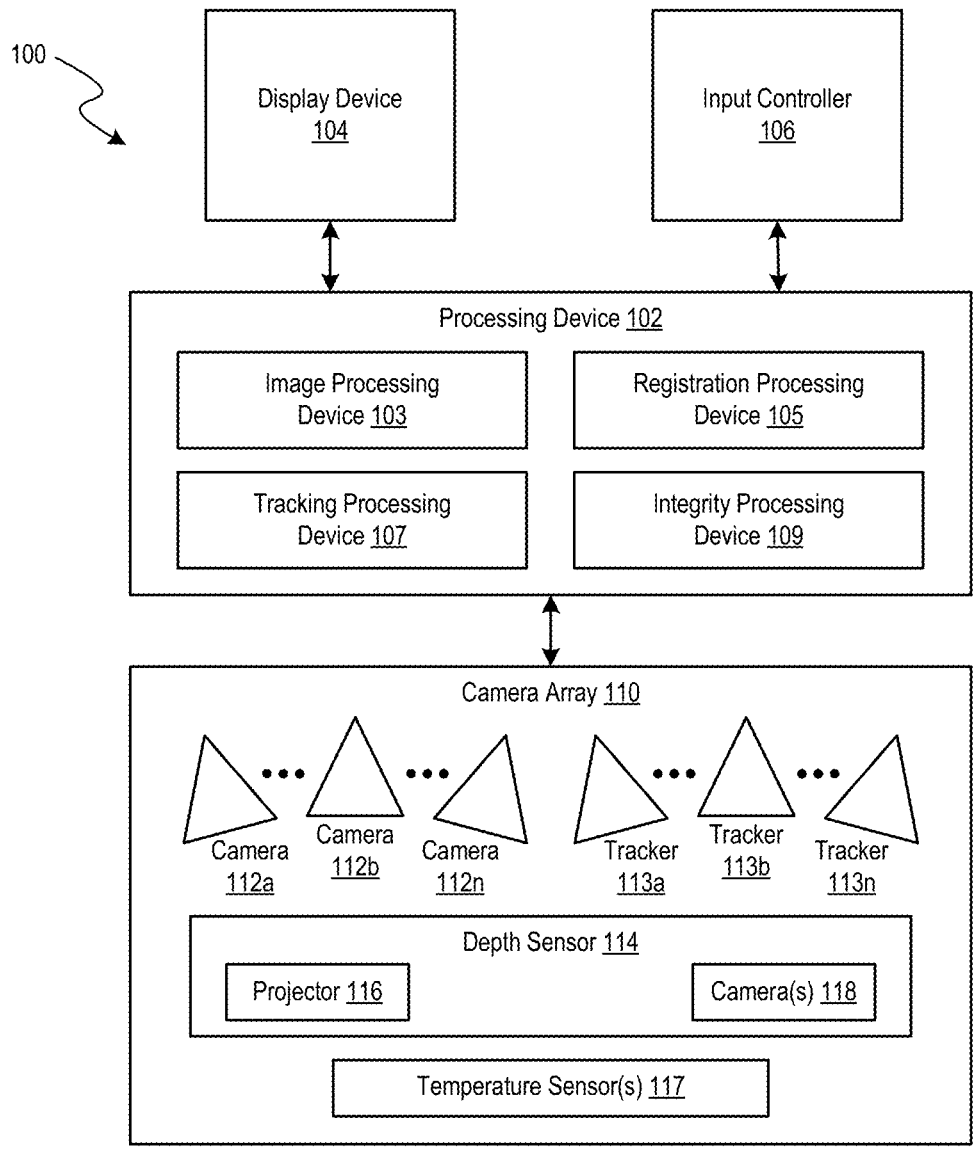
FIG. 1 is a schematic view of an imaging system in accordance with embodiments of the present technology.
Figure 1:
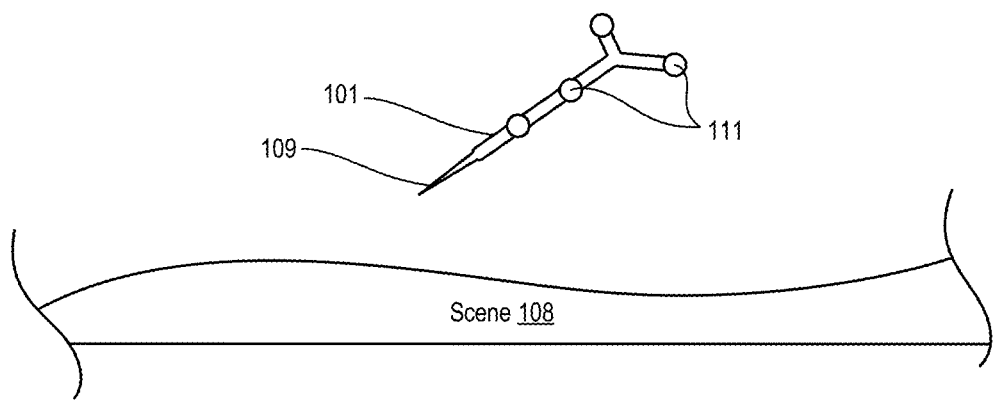

Aspects of the present disclosure are directed generally to data capture, storage, distribution, and replay associated mediated-reality imaging systems or standard two-dimensional display systems. In several of the embodiments described below, for example, an imaging system includes a camera array configured to capture multiple images of a scene. Each of the multiple images includes color data represented in a Bayer pattern that includes a blue channel, two green channels, and a red channel. The imaging system also includes an image processing device configured to receive the multiple images captured by the camera array, split each of the multiple images represented in the Bayer pattern into four individual color planes, form at least one set of data by combining the four individual color planes of the multiple images, and compress at least one set of data. In some embodiments, at least one set of data is formed by stacking the four individual color planes of each of the multiple images. As another example, a method for generating a ledger for data captured during a medical procedure includes determining an event associated with the medical procedure, generating an event block using data associated with the event, wherein the event block is associated with a unique identifier generated based on data of the event, and appending the event block to a chain of blocks representing events that have occurred in the medical procedure.

Specific details of several embodiments of the present technology are described herein with reference to FIGS. 1-12. The present technology, however, can be practiced without some of these specific details. In some instances, well-known structures and techniques often associated with camera arrays, light field cameras, image reconstruction, registration process, and the like have not been shown in detail so as not to obscure the present technology.

The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

The headings provided herein are for convenience only and should not be construed as limiting the subject matter disclosed. To the extent any materials incorporated herein by reference conflict with the present disclosure, the present disclosure controls.

Selected Embodiments of Imaging Systems

FIG. 1 is a schematic view of an imaging system 100 ("system 100") in accordance with embodiments of the present technology. In some embodiments, the system 100 can be a synthetic augmented reality system, a virtual-reality imaging system, an augmented-reality imaging system, a mediated-reality imaging system, and/or a non-immersive computational imaging system. In the illustrated embodiment, the system 100 includes a processing device 102 that is communicatively coupled to one or more display devices 104, one or more input controllers 106, and a camera array 110. In other embodiments, the system 100 can comprise additional, fewer, or different components. In some embodiments, the system 100 includes some features that are generally similar or identical to those of the mediated-reality imaging systems disclosed in (i) U.S. patent application Ser. No. 16/586,375, titled "CAMERA ARRAY FOR A MEDIATED-REALITY SYSTEM," and filed Sep. 27, 2019 and/or (ii) U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," and filed May 12, 2020, each of which is incorporated herein by reference in its entirety.

In the illustrated embodiment, the camera array 110 includes a plurality of cameras 112 (identified individually as cameras 112a-112n; which can also be referred to as first cameras) that can each capture images of a scene 108 (e.g., first image data) from a different perspective. The scene 108 can include for example, a patient undergoing surgery (e.g., spinal surgery) and/or another medical procedure. In other embodiments, the scene 108 can be another type of scene, including other types of target object(s) or surface(s). The camera array 110 can further include dedicated object tracking hardware 113 (e.g., including individually identified trackers 113a-113n; which can also be referred to as second cameras) that captures positional data of one or more objects, such as the tip 109 of an instrument 101 (e.g., a surgical instrument or tool) to track the movement and/or orientation of the objects through/in the scene 108. In some embodiments, the cameras 112 and the trackers 113 are positioned at fixed locations and orientations (e.g., poses) relative to one another. For example, the cameras 112 and the trackers 113 can be structurally secured by/to a mounting structure (e.g., a frame) at predefined fixed locations and orientations. In some embodiments, the cameras 112 are positioned such that neighboring cameras 112 share overlapping views of the scene 108. In general, the position of the cameras 112 can be selected to maximize clear and accurate capture of all or a selected portion of the scene 108. Likewise, the trackers 113 can be positioned such that neighboring trackers 113 share overlapping views of the scene 108. Therefore, all or a subset of the cameras 112 and the trackers 113 can have different extrinsic parameters, such as position and orientation.

In some embodiments, the cameras 112 in the camera array 110 are synchronized to capture images of the scene 108 simultaneously (within a threshold temporal error). In some embodiments, all or a subset of the cameras 112 are light field/plenoptic/color cameras that capture information about the light field emanating from the scene 108 (e.g., information about the intensity of light rays in the scene 108 and also information about a direction the light rays are traveling through space). A light field camera is a camera that captures information about the light field emanating from a scene. That is, the camera captures the precise direction that the light rays travel in space, thereby allowing adjustment of the depth of field and refocusing of the images. Therefore, in some embodiments, the images captured by the cameras 112 encode depth information representing a surface geometry of the scene 108.

In some embodiments, the cameras 112 are substantially identical. In other embodiments, the cameras 112 include multiple cameras of different types. For example, different subsets of the cameras 112 can have different intrinsic parameters such as focal length, sensor type, optical components, and the like. The cameras 112 can have charge-coupled device (CCD) and/or complementary metal-oxide semiconductor (CMOS) image sensors and associated optics. Such optics can include a variety of configurations including lensed or bare individual image sensors in combination with larger macro lenses, micro-lens arrays, prisms, and/or negative lenses. For example, the cameras 112 can be separate light field cameras each having their own image sensors and optics. In other embodiments, some or all of the cameras 112 can comprise separate microlenslets (e.g., lenslets, lenses, microlenses) of a microlens array (MLA) that share a common image sensor.

In some embodiments, the trackers 113 are imaging devices, such as infrared (IR) cameras that can capture images of the scene 108 from a different perspective compared to other ones of the trackers 113. Accordingly, the trackers 113 and the cameras 112 can have different spectral sensitives (e.g., infrared vs. visible wavelength). In some embodiments, the trackers 113 capture image data of a plurality of optical markers (e.g., fiducial markers, marker balls) in the scene 108, such as markers 111 coupled to the instrument 101.

In the illustrated embodiment, the camera array 110 further includes a depth sensor 114. In some embodiments, the depth sensor 114 includes (i) one or more projectors 116 that project a structured light pattern onto/into the scene 108 and (ii) one or more depth cameras 118 (which can also be referred to as second cameras) that capture second image data of the scene 108 including the structured light projected onto the scene 108 by the projector 116. The projector 116 and the depth cameras 118 can operate in the same wavelength and, in some embodiments, can operate in a wavelength different than the cameras 112. For example, the cameras 112 can capture the first image data in the visible spectrum, while the depth cameras 118 capture the second image data in the infrared spectrum. In some embodiments, the depth cameras 118 have a resolution that is less than a resolution of the cameras 112. For example, the depth cameras 118 can have a resolution that is less than 70%, 60%, 50%, 40%, 30%, or 20% of the resolution of the cameras 112. In other embodiments, the depth sensor 114 can include other types of dedicated depth detection hardware (e.g., a LiDAR detector) for determining the surface geometry of the scene 108. In other embodiments, the camera array 110 can omit the projector 116 and/or the depth cameras 118.

In the illustrated embodiment, the processing device 102 includes an image processing device 103 (e.g., an image processor, an image processing module, an image processing unit), a registration processing device 105 (e.g., a registration processor, a registration processing module, a registration processing unit), a tracking processing device 107 (e.g., a tracking processor, a tracking processing module, a tracking processing unit), and an integrity processing device 109 (e.g., an integrity processor, an integrity processing module, an integrity processing unit). The image processing device 103 can (i) receive the first image data captured by the cameras 112 (e.g., light field images, hyperspectral images, light field image data, RGB images, hyperspectral images) and depth information from the depth sensor 114 (e.g., the second image data captured by the depth cameras 118), and (ii) process the image data and depth information to synthesize (e.g., generate, reconstruct, render) a three-dimensional (3D) output image of the scene 108 corresponding to a virtual camera perspective. The output image can correspond to an approximation of an image of the scene 108 that would be captured by a camera placed at an arbitrary position and orientation corresponding to the virtual camera perspective. In some embodiments, the image processing device 103 can further receive and/or store calibration data for the cameras 112 and/or the depth cameras 118 and synthesize the output image based on the image data, the depth information, and/or the calibration data. More specifically, the depth information and the calibration data can be used/combined with the images from the cameras 112 to synthesize the output image as a 3D (or stereoscopic 2D) rendering of the scene 108 as viewed from the virtual camera perspective. In some embodiments, the image processing device 103 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," and filed Jun. 28, 2019, which is incorporated herein by reference in its entirety. In other embodiments, the image processing device 103 can generate the virtual camera perspective based only on the images captured by the cameras 112—without utilizing depth information from the depth sensor 114. For example, the image processing device 103 can generate the virtual camera perspective by interpolating between the different images captured by one or more of the cameras 112.

The image processing device 103 can synthesize the output image from images captured by a subset (e.g., two or more) of the cameras 112 in the camera array 110, and does not necessarily utilize images from all of the cameras 112. For example, for a given virtual camera perspective, the processing device 102 can select a stereoscopic pair of images from two of the cameras 112. In some embodiments, such a stereoscopic pair can be selected to be positioned and oriented to most closely match the virtual camera perspective. In some embodiments, the image processing device 103 (and/or the depth sensor 114) estimates a depth for each surface point of the scene 108 relative to a common origin to generate a point cloud and/or a 3D mesh that represents the surface geometry of the scene 108. Such a representation of the surface geometry can be referred to as a depth map, an N35 surface, a depth surface, and/or the like. In some embodiments, the depth cameras 118 of the depth sensor 114 detect the structured light projected onto the scene 108 by the projector 116 to estimate depth information of the scene 108. In some embodiments, the image processing device 103 estimates depth from multiview image data from the cameras 112 using techniques such as light field correspondence, stereo block matching, photometric symmetry, correspondence, defocus, block matching, texture-assisted block matching, structured light, and the like, with or without utilizing information collected by the depth sensor 114. In other embodiments, depth may be acquired by a specialized set of the cameras 112 performing the aforementioned methods in another wavelength.

In some embodiments, the registration processing device 105 receives and/or stores previously-captured or initial image data, such as image data of a three-dimensional volume of a patient (3D image data). The image data can include, for example, computerized tomography (CT) scan data, magnetic resonance imaging (MRI) scan data, ultrasound images, fluoroscope images, and/or other medical or other image data. The registration processing device 105 can register the initial image data to the real-time images captured by the cameras 112 and/or the depth sensor 114 by, for example, determining one or more transforms/transformations/mappings between the two. The processing device 102 (e.g., the image processing device 103) can then apply the one or more transforms to the initial image data such that the initial image data can be aligned with (e.g., overlaid on) the output image of the scene 108 in real-time or near real-time on a frame-by-frame basis, even as the virtual perspective changes. That is, the image processing device 103 can fuse the initial image data with the real-time output image of the scene 108 to present a mediated-reality view that enables, for example, a surgeon to simultaneously view a surgical site in the scene 108 and the underlying 3D anatomy of a patient undergoing an operation. In some embodiments, the registration processing device 105 can register the previously-captured image data to the real-time images using any of the methods disclosed in U.S. patent application Ser. No. 17/140,885, titled "METHODS AND SYSTEMS FOR REGISTERING PREOPERATIVE IMAGE DATA TO INTRAOPERATIVE IMAGE DATA OF A SCENE, SUCH AS A SURGICAL SCENE," and filed Jan. 4, 2021.

In some embodiments, the tracking processing device 107 processes positional data captured by the trackers 113 to track objects (e.g., the instrument 101) within the vicinity of the scene 108. For example, the tracking processing device 107 can determine the position of the markers 115 in the 2D images captured by two or more of the trackers 113, and can compute the 3D position of the markers 115 via triangulation of the 2D positional data. More specifically, in some embodiments the trackers 113 include dedicated processing hardware for determining positional data from captured images, such as a centroid of the markers 115 in the captured images. The trackers 113 can then transmit the positional data to the tracking processing device 107 for determining the 3D position of the markers 115. In other embodiments, the tracking processing device 107 can receive the raw image data from the trackers 113. In a surgical application, for example, the tracked object can comprise a surgical instrument, an implant, a hand or arm of a physician or assistant, and/or another object having the markers 115 mounted thereto. In some embodiments, the processing device 102 can recognize the tracked object as being separate from the scene 108, and can apply a visual effect to the 3D output image to distinguish the tracked object by, for example, highlighting the object, labeling the object, and/or applying a transparency to the object. The translational and rotational positions of the instruments and/or tools, along with the 3D representation of the scene (e.g., the 3D mesh), can enable the recreation of the medical procedure and enable replay of the data from a different perspective that was not available during the procedure.

In some embodiments, the integrity processing device 109 process the data captured by the camera array 110 and produces a ledger of events. The ledger includes multiple blocks, each associated with a unique identifier of the block representing an event that has occurred during capturing of the scene. Each event block maintains its integrity by using the data within that event block to validate itself as part of the chain, thereby ensuring that blocks within a chain have not been tampered with and that its integrity is maintained.

In some embodiments, functions attributed to the processing device 102, the image processing device 103, the registration processing device 105, the tracking processing device 107, and/or the alignment processing device 109 can be practically implemented by two or more physical devices. For example, in some embodiments a synchronization controller (not shown) controls images displayed by the projector 116 and sends synchronization signals to the cameras 112 to ensure synchronization between the cameras 112 and the projector 116 to enable fast, multi-frame, multicamera structured light scans. Additionally, such a synchronization controller can operate as a parameter server that stores hardware specific configurations such as parameters of the structured light scan, camera settings, and camera calibration data specific to the camera configuration of the camera array 110. The synchronization controller can be implemented in a separate physical device from a display controller that controls the display device 104, or the devices can be integrated together.

The processing device 102 can comprise a processor and a non-transitory computer-readable storage medium that stores instructions that when executed by the processor, carry out the functions attributed to the processing device 102 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the present technology described below can be stored or distributed on computer-readable media, including magnetic and optically readable and removable computer discs, stored as in chips (e.g., EEPROM or flash memory chips). Alternatively, aspects of the present technology can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the present technology.

The virtual camera perspective is controlled by an input controller 106 that can update the virtual camera perspective based on user driven changes to the camera's position and rotation. The output images corresponding to the virtual camera perspective can be outputted to the display device 104. In some embodiments, the image processing device 103 can vary the perspective, the depth of field (e.g., aperture), the focus plane, and/or another parameter of the virtual camera (e.g., based on an input from the input controller) to generate different 3D output images without physically moving the camera array 110. The display device 104 can receive output images (e.g., the synthesized 3D rendering of the scene 108) and display the output images for viewing by one or more viewers. In some embodiments, the processing device 102 receives and processes inputs from the input controller 106 and processes the captured images from the camera array 110 to generate output images corresponding to the virtual perspective in substantially real-time or near real-time as perceived by a viewer of the display device 104 (e.g., at least as fast as the frame rate of the camera array 110).

Additionally, the display device 104 can display a graphical representation on/in the image of the virtual perspective of any (i) tracked objects within the scene 108 (e.g., a surgical instrument) and/or (ii) registered or unregistered initial image data. That is, for example, the system 100 (e.g., via the display device 104) can blend augmented data into the scene 108 by overlaying and aligning information on top of "passthrough" images of the scene 108 captured by the cameras 112. Moreover, the system 100 can create a mediated-reality experience where the scene 108 is reconstructed using light field image date of the scene 108 captured by the cameras 112, and where instruments are virtually represented in the reconstructed scene via information from the trackers 113. Additionally or alternatively, the system 100 can remove the original scene 108 and completely replace it with a registered and representative arrangement of the initially captured image data, thereby removing information in the scene 108 that is not pertinent to a user's task.

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. In some embodiments, the system 100 can further include a separate tracking system (not shown), such an optical tracking system, for tracking the display device 104, the instrument 101, and/or other components within the scene 108. Such a tracking system can detect a position of the head-mounted display device 104 and input the position to the input controller 106. The virtual camera perspective can then be derived to correspond to the position and orientation of the head-mounted display device 104 in the same reference frame and at the calculated depth (e.g., as calculated by the depth sensor 114) such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller) that enables a viewer to manually control the virtual perspective displayed by the display device 104.

Figure 2A:
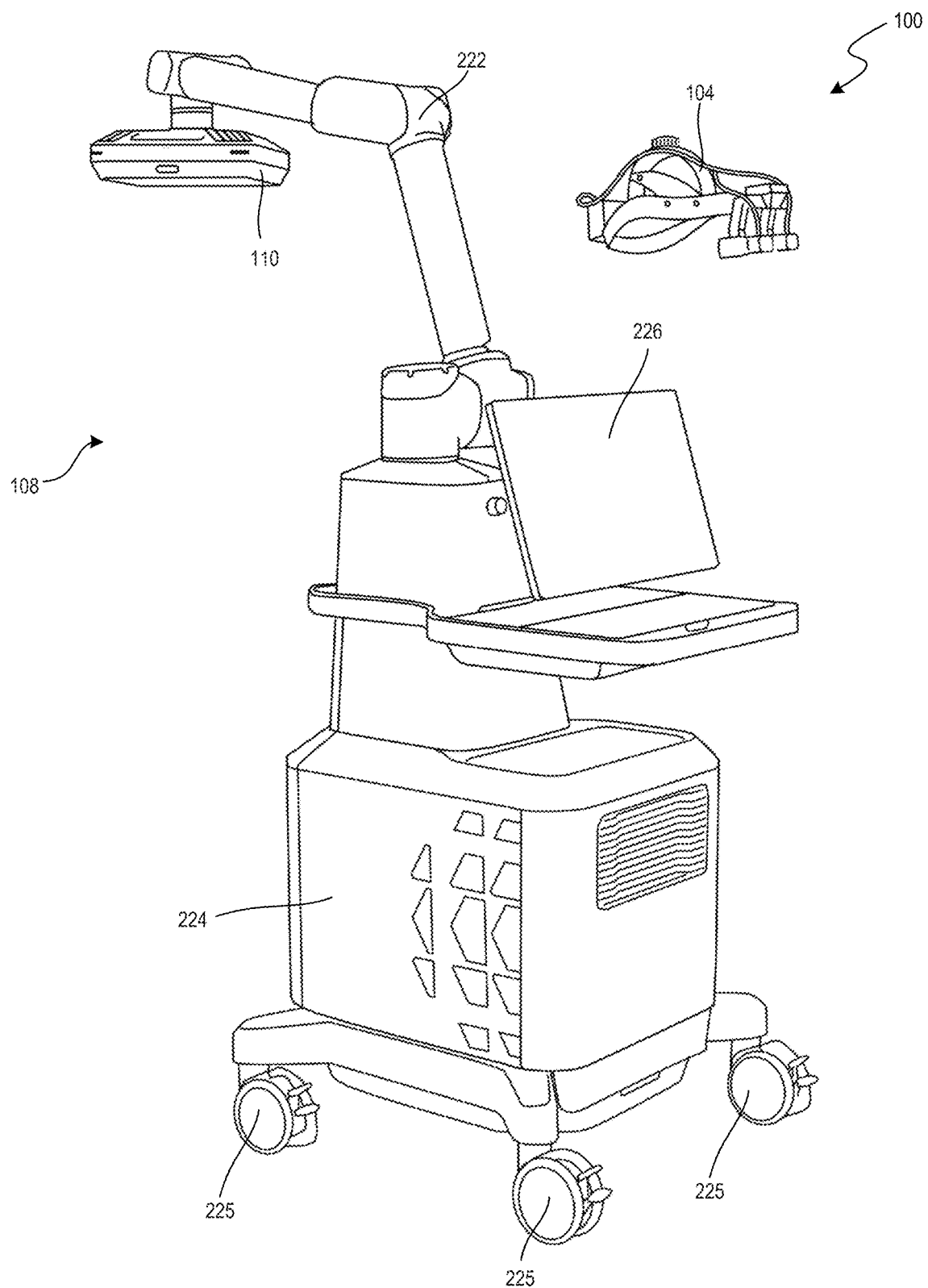
FIG. 2A is a perspective view of a surgical environment employing the imaging system of FIG. 1 for a surgical application in accordance with embodiments of the present technology.

FIG. 2A is a perspective view of a surgical environment employing the system 100 for a surgical application in accordance with embodiments of the present technology. In the illustrated embodiment, the camera array 110 is positioned over the scene 108 (e.g., a surgical site) and supported/positioned via a movable arm 222 that is operably coupled to a workstation 224. In some embodiments, the arm 222 is manually movable to position the camera array 110 while, in other embodiments, the arm 222 is robotically controlled in response to the input controller 106 (FIG. 1) and/or another controller. In the illustrated embodiment, the workstation 224 is mounted on wheels or casters 225 that allow the system 100 to be rolled. In some embodiments, the system 100 can be rolled on the casters 225 and/or the arm 222 can be moved to scan a region of the scene 108, such as a portion of a patient's spine.

In the illustrated embodiment, the display device 104 is a head-mounted display device (e.g., a virtual reality headset, augmented reality headset). The workstation 224 can include a computer to control various functions of the processing device 102, the display device 104, the input controller 106, the camera array 110, and/or other components of the system 100 shown in FIG. 1. Accordingly, in some embodiments the processing device 102 and the input controller 106 are each integrated in the workstation 224. In some embodiments, the workstation 224 includes a secondary display 226 that can display a user interface for performing various configuration functions, a mirrored image of the display on the display device 104, and/or other useful visual images/indications. In other embodiments, the system 100 can include more or fewer display devices. For example, in addition to the display device 104 and the secondary display 226, the system 100 can include another display (e.g., a medical grade computer monitor) visible to the user wearing the display device 104.

Figure 2B:
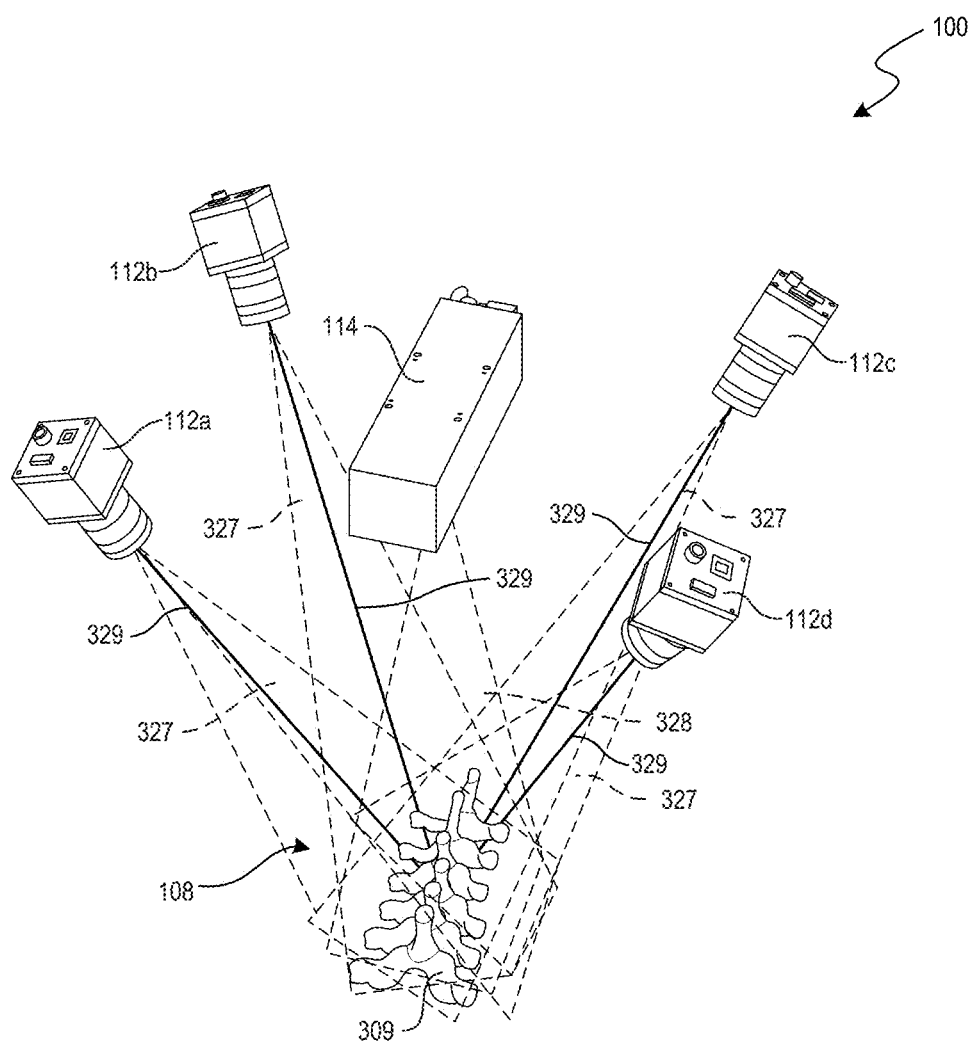
FIG. 2B is an isometric view of a portion of the imaging system of FIG. 1 illustrating four cameras of the imaging system in accordance with embodiments of the present technology.

FIG. 2B is an isometric view of a portion of the system 100 illustrating four of the cameras 112 in accordance with embodiments of the present technology. Other components of the system 100 (e.g., other portions of the camera array 110, the processing device 102, etc.) are not shown in FIG. 3 for the sake of clarity. In the illustrated embodiment, each of the cameras 112 has a field of view 327 and a focal axis 329. Likewise, the depth sensor 114 can have a field of view 328 aligned with a portion of the scene 108. The cameras 112 can be oriented such that the fields of view 327 are aligned with a portion of the scene 108 and at least partially overlap one another to together define an imaging volume. In some embodiments, some or all of the field of views 327, 328 at least partially overlap. For example, in the illustrated embodiment the fields of view 327, 328 converge toward a common measurement volume including a portion of a spine 309 of a patient (e.g., a human patient) located in/at the scene 108. In some embodiments, the cameras 112 are further oriented such that the focal axes 329 converge to a common point in the scene 108. In some aspects of the present technology, the convergence/alignment of the focal axes 329 can generally maximize disparity measurements between the cameras 112. In some embodiments, the cameras 112 and the depth sensor 114 are fixedly positioned relative to one another (e.g., rigidly mounted to a common frame) such that the positions of the cameras 112 and the depth sensor 114 relative to one another is known and/or can be readily determined via a calibration process. In other embodiments, the system 100 can include a different number of the cameras 112 and/or the cameras 112 can be positioned differently relative to another. In some embodiments, the camera array 110 can be moved (e.g., via the arm 222 of FIG. 2) to move the fields of view 327, 328 to, for example, scan the spine 309.

Referring to FIGS. 1-2B together, in some aspects of the present technology the system 100 can generate a digitized view of the scene 108 that provides a user (e.g., a surgeon) with increased "volumetric intelligence" of the scene 108. For example, the digitized scene 108 can be presented to the user from the perspective, orientation, and/or viewpoint of their eyes such that they effectively view the scene 108 as though they were not viewing the digitized image (e.g., as though they were not wearing the head-mounted display 104). However, the digitized scene 108 permits the user to digitally rotate, zoom, crop, or otherwise enhance their view to, for example, facilitate a surgical workflow. Likewise, initial image data, such as CT scans, can be registered to and overlaid over the image of the scene 108 to allow a surgeon to view these data sets together. Such a fused view can allow the surgeon to visualize aspects of a surgical site that may be obscured in the physical scene 108—such as regions of bone and/or tissue that have not been surgically exposed.

Selected Embodiments of Data Storage

Figure 3:
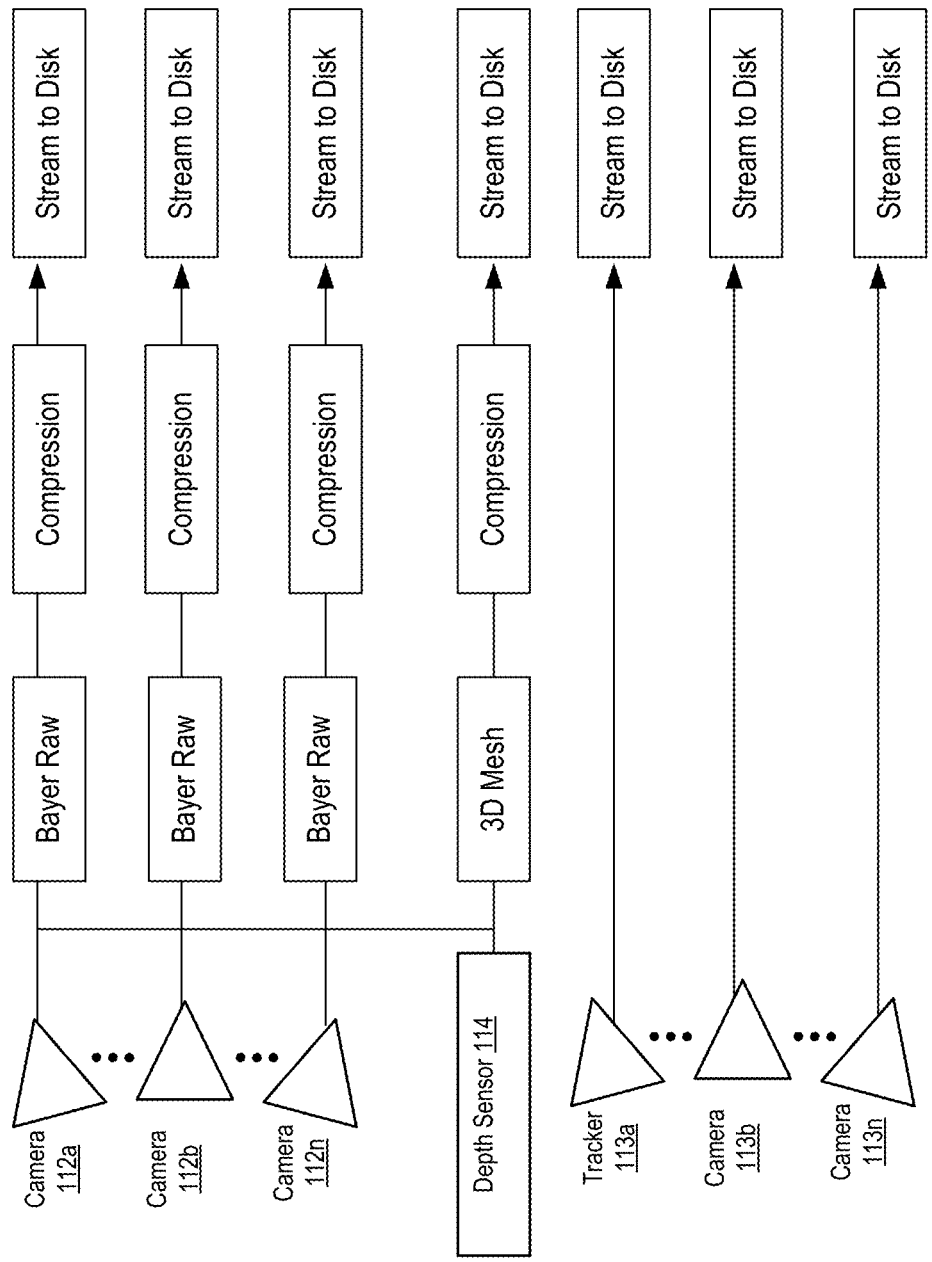
FIG. 3 is a schematic diagram of example data streams from an imaging system in accordance with embodiments of the present technology.

Capturing and processing data received simultaneously from different types of sources (e.g., camera arrays, depth sensors, trackers), however, can lead to difficulties in the efficient storage or streaming of the data (locally and/or remotely in the cloud). FIG. 3 is a schematic diagram of example data streams from the system 100 in accordance with embodiments of the present technology. As shown in FIG. 3, each of the cameras 112a-112n in the camera array produces a stream of raw image data, which is compressed and then streamed to the disk or the cloud. The image data can also be combined with the depth information produced by the depth sensor 114 to synthesize the 3D output mesh of the scene. The 3D mesh can be compressed and streamed to the disk or the disk. Because the light field includes spatial and angular information of the light captured from a scene and is typically recorded as a combination of images and point cloud/depth data, the volume of data poses significant challenges to real-time operations (e.g., synthesis, storage, display, etc.). In addition, auxiliary data such as tool tracking, sensor inputs and/or voice captures are also streamed to the disk or the cloud to facilitate the display and playback of the recorded scene. For example, as shown in FIG. 3, each of the trackers 113a-113n produces separate tracking information. It is desirable to process and simultaneously display onto the display device 104 (FIG. 1) data collected from different types of sources, while also ensuring a good image quality and a high frame rate required for some surgical operations. Furthermore, there remains a need to enable remote processing and distribution of the data (e.g., for consultation purposes) and playback at external locations (e.g., for educational, legal, insurance coverage or other purposes).

This patent document discloses techniques that can be implemented in various embodiments to enable efficient and compact storage of different types of data (e.g., color/depth data from the cameras and/or the depth sensor, as well as auxiliary data), thereby minimizing data footprint and reducing latencies in data streaming that occur during system operation. The disclosed techniques enable real-time or near real-time capture and reconstruction of the light field data. The disclosed techniques can also be implemented to ensure patient data integrity when the data is transferred (e.g., imported and/or exported) among different systems.

Some examples of the disclosed techniques are further described below. Section headings are used in the present document only to improve readability and do not limit scope of the disclosed embodiments and techniques in each section to only that section.

Red-Green-Blue (RGB) Data Storage

Figure 4:
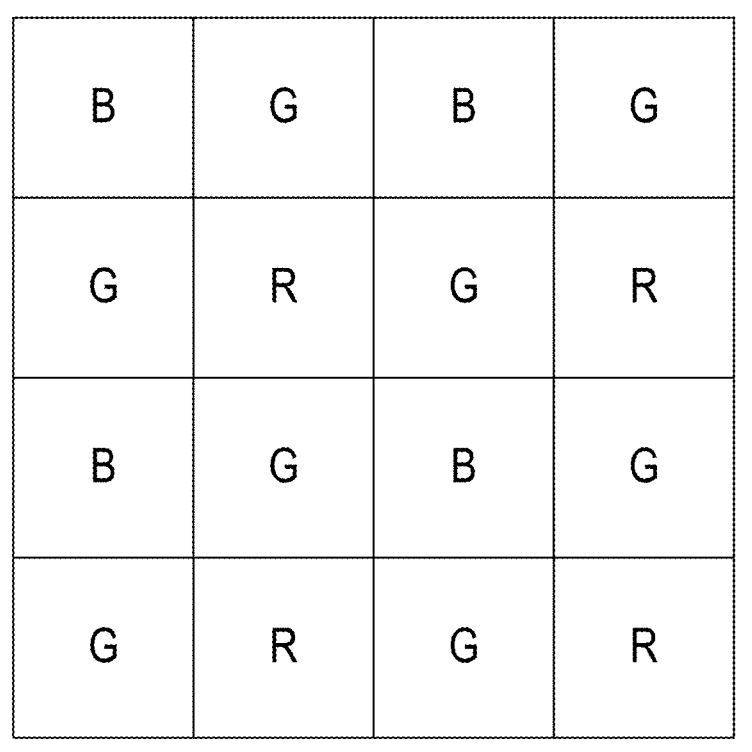

The output of the camera array 110 includes RGB data that represents the color and intensity of the light for each pixel. In some embodiments, the RGB data is captured in a Bayer pattern generated by a Bayer filter that filters a square grid of photosensors. FIG. 4 illustrates an example four-color 2×2 Bayer pattern known as a Color Filter Array (CFA). The Bayer pattern is half green, one quarter red, and one quarter blue, including a Blue (B) channel, two Green (G) channels, and a Red (R) channel. Each channel records the intensity of light for one of the three colors at a specified camera bit resolution (e.g., 8, 10, or 12 bits). To obtain a full-color image, various de-mosaicking algorithms can be used to interpolate a set of complete red, green, and blue values for each pixel using the surrounding pixels of the corresponding colors.

Figure 5:
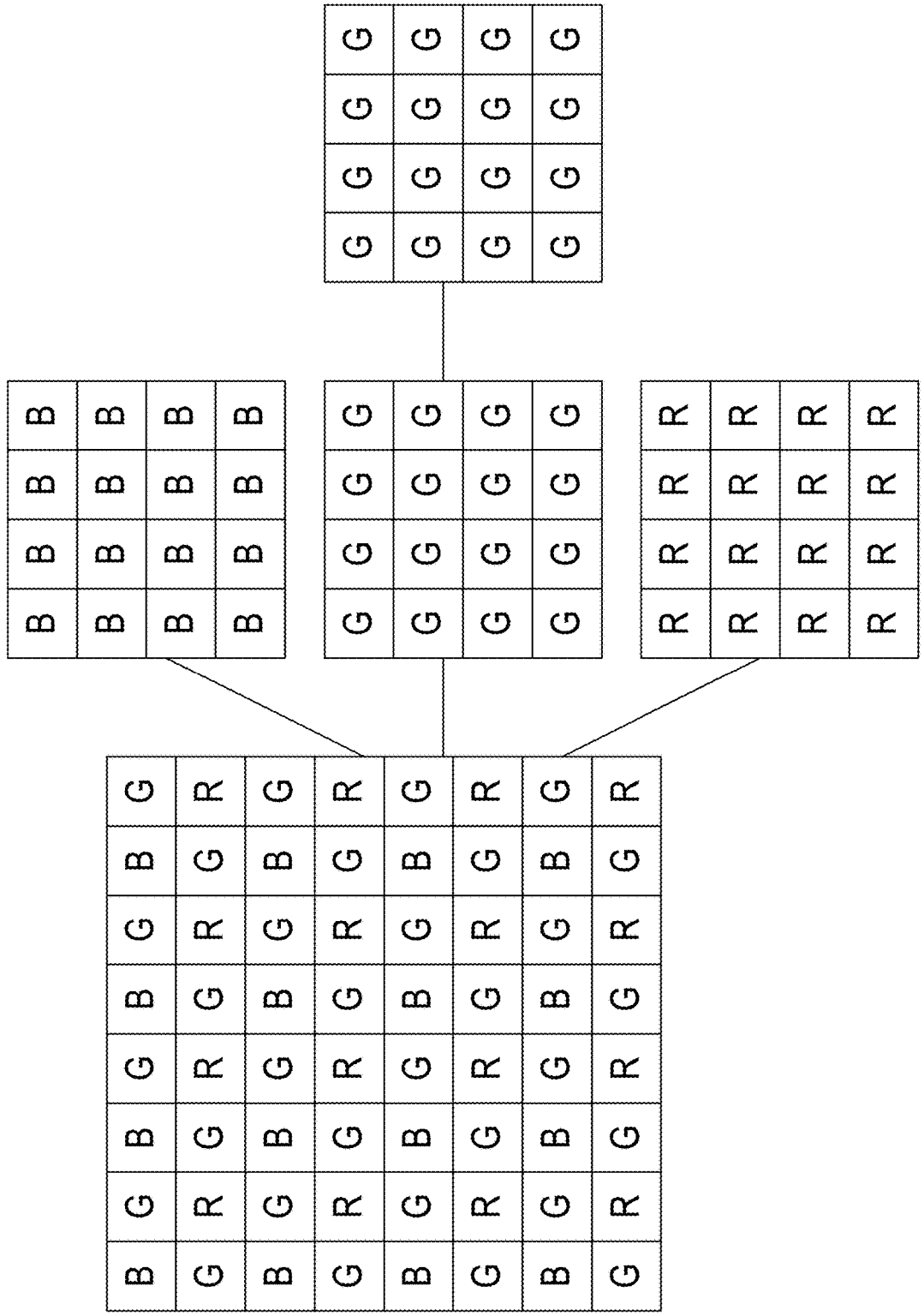
FIG. 5 illustrates an example way of splitting a Bayer pattern into individual color planes in accordance with embodiments of the present technology.

The Bayer pattern is one of the most compact representation of the raw data prior to compression. The compression quality and rate of the Bayer pattern, however, are suboptimal because the Bayer image has sharp discontinuities between pixels representing different color channels. Such discontinuities effectively get blurred in the compression process, resulting in data loss and low Peak Signal-to-Noise Ratio (PSNR). To address the discontinuities between the pixels, one approach is to split the Bayer pattern into individual color planes. FIG. 5 illustrates an example method of splitting a Bayer pattern into individual color planes in accordance with embodiments of the present technology. As shown in FIG. 5, an 8×8 Bayer pattern can be split into four 4×4 color planes. The individual color planes can be subsequently combined (e.g., stacked) to minimize the discontinuities among pixels before being compressed.

Figure 6A:
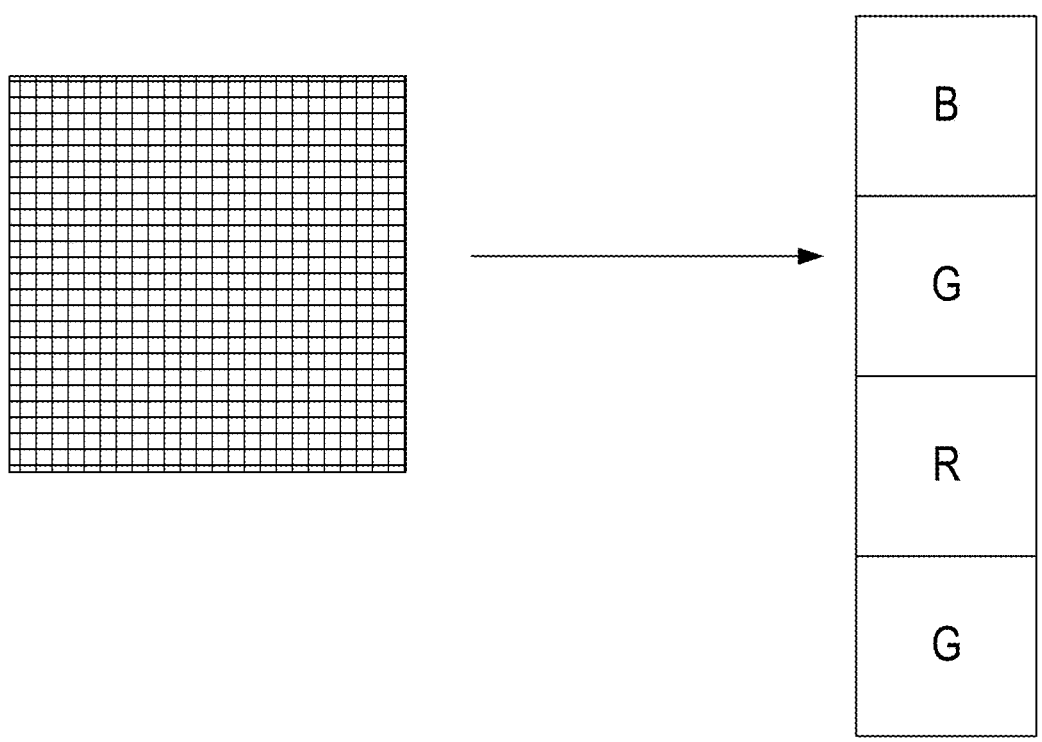
FIG. 6A illustrates an example way of organizing the individual color channels in accordance with embodiments of the present technology.
Figure 6B:
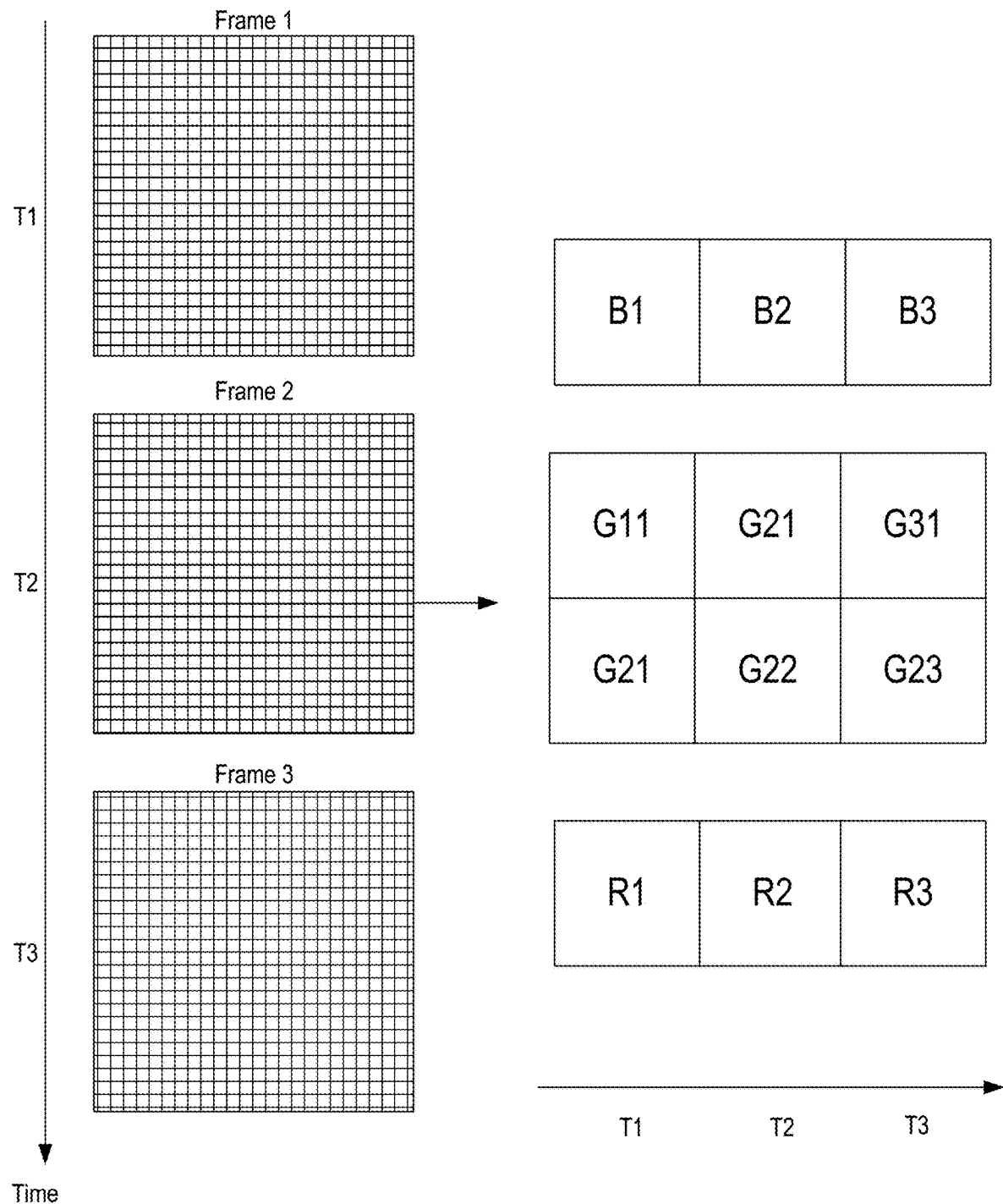
FIG. 6B illustrates another example way of organizing the individual color channels in accordance with embodiments of the present technology.
Figure 6C:
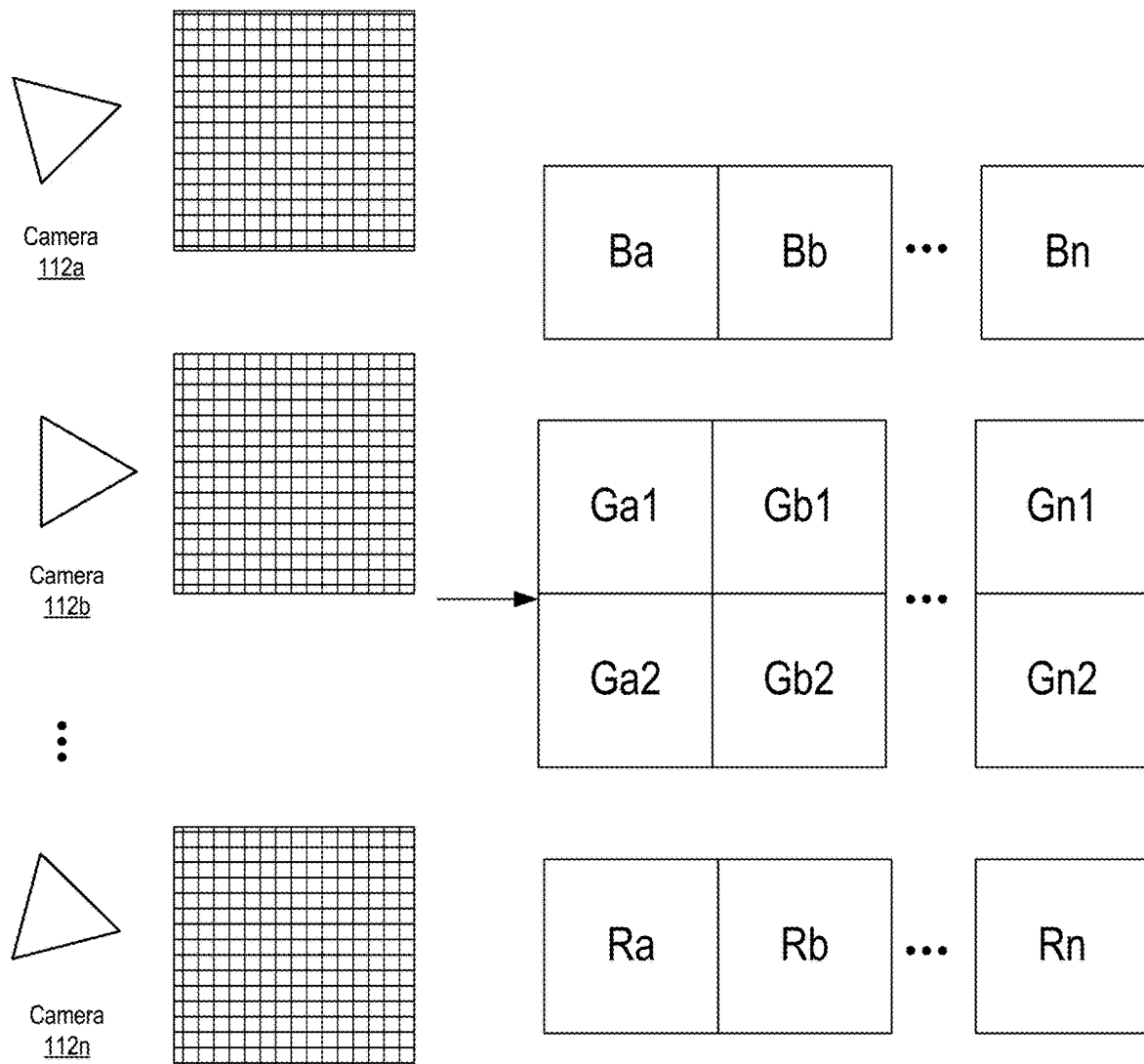
FIG. 6C illustrates yet another example way of organizing the individual color channels in accordance with embodiments of the present technology.

FIGS. 6A-C illustrate example methods of combining the individual color channels in accordance with embodiments of the present technology. In the example shown in FIG. 6A, the two green channels are separated by either the red or the blue channels. The stacked data representing the original frame is then compressed using techniques such as the Joint Photographic Experts Group (JPEG) compression techniques. It is noted that JPEG compression techniques are only applicable to color images. For luminous images (e.g., gray level images), the two unused channels are left as empty images and compress to near zero length. Using the disclosed techniques such as shown in FIG. 6A, the discontinuity in pixel values is addressed by separating the color planes.

The individual color planes can also be combined to obtain a temporal or spatial coherence in the image data. For example, as shown in FIG. 6B, in some embodiments, different Bayer pattern frames captured at different times in the temporal domain (e.g., Frame 1 captured at T1, Frame 2 captured at T2, Frame 3 captured at T3) can be split and combined according to the color planes. For example, the blue color planes of Frame 1, Frame 2, and Frame 3 are grouped together temporally (e.g., B1 to B3), and the red color planes of Frame 1, Frame 2, and Frame 3 are grouped together temporally (e.g., R1 to R3). The two green planes of Frame 1, Frame 2, and Frame 3 can be grouped together as shown in FIG. 6B (e.g., G11 to G23), or separately to two sets of data similar to the blue or red color plane (e.g., G11 to G31, and G21 to G23). The individual color planes can then be compressed separately using compression techniques such as the JPEG compression. Because each stream of the color plane includes information that is temporally co-located (e.g., motion information present in consecutive frames), additional compression techniques that take advantage of the motion compensation techniques (e.g., optical flow) can be combined to improve the efficiency of the data compression. In some embodiments, metadata (e.g., time-stamp of the frames) can be included in each compressed single-channel frame to allow efficient decompression and de-mosaicking of the images.

FIG. 6C illustrates another example method in which different Bayer pattern frames from different cameras (e.g., Camera 1, Camera 2, Camera 3) captured at the same time (e.g., at time T1) are split and combined together according to the color planes. The blue color planes of images captured at time T1 by cameras 112a-112n can be grouped together (e.g., Ba, Bb, . . . , Bn). The red color planes of the images captured at T1 by cameras 112a-112n can be grouped together (e.g., Ra, Rb, . . . , Rn). The two green planes of the images captured by cameras 112a-112b can be grouped together as shown in FIG. 6C (e.g., Ga1 to Gn2), or separately into two sets of data in a manner similar to the blue color plane (e.g., Ga1 to Gn1, Ga2 to Gn2). Because different cameras capture the same scene under different angles, the frames from these cameras are spatially coherent and include redundancies that can be discarded during the compression process, leading to improved compression rates. In some embodiments, metadata (e.g., camera identifier) can be included in each compressed single-channel frame to allow efficient decompression and de-mosaicking of the images.

Table 1 shows an example compression performance between direct compression of Bayer raw images (standard JPEG compression) and compression using the disclosed techniques. As shown in Table 1, both the compression ratio and the PSNR values are improved as compared to the conventional Bayer compression techniques.

TABLE 1

Example Compression Performance Comparison

| Image | PNG size Bytes | Bayer compress Bytes | Std. compress Bytes | Bayer ratio % | Std ratio % | Std/ Bayer | Bayer PSNR | Bayer SSIM | Std PSNR | Std SSIM |
|---|---|---|---|---|---|---|---|---|---|---|
| 1 | 6134784 | 1042432 | 2171904 | 88.48 | 76.00 | 2.08 | 42.633 | 0.9804 | 39.587 | 0.9515 |
| 2 | 5364736 | 886784 | 1688576 | 90.20 | 81.34 | 1.90 | 44.457 | 0.9839 | 40.694 | 0.9502 |

TABLE 1-continued

Example Compression Performance Comparison

| Image | PNG size Bytes | Bayer compress Bytes | Std. compress Bytes | Bayer ratio % | Std ratio % | Std/ Bayer | Bayer PSNR | Bayer SSIM | Std PSNR | Std SSIM |
|---|---|---|---|---|---|---|---|---|---|---|
| 3 | 7471204 | 1836032 | 3220480 | 79.71 | 64.41 | 1.75 | 40.865 | 0.9916 | 38.486 | 0.9798 |
| 4 | 7173120 | 1405952 | 2231296 | 84.46 | 75.34 | 1.59 | 41.343 | 0.9898 | 39.135 | 0.9732 |
| 5 | 7747584 | 1683456 | 3506176 | 81.39 | 61.25 | 2.08 | 40.456 | 0.9939 | 38.406 | 0.9858 |
| 6 | 6480896 | 1208320 | 2361344 | 86.65 | 73.90 | 1.95 | 42.620 | 0.9901 | 40.043 | 0.9753 |
| 7 | 7513088 | 1757184 | 3246080 | 80.58 | 64.12 | 1.85 | 40.327 | 0.9889 | 38.415 | 0.9779 |
| 8 | 6063104 | 1335296 | 2136064 | 85.24 | 76.39 | 1.60 | 42.677 | 0.9841 | 39.904 | 0.9606 |
| 9 | 6553600 | 1296384 | 2922496 | 85.67 | 67.70 | 2.25 | 41.539 | 0.9918 | 39.013 | 0.9815 |
| 10 | 5826560 | 1005568 | 1899520 | 88.89 | 79.01 | 1.89 | 43.544 | 0.9874 | 40.643 | 0.9655 |
| 11 | 6512640 | 1373184 | 2772992 | 84.82 | 69.35 | 2.02 | 41.466 | 0.9870 | 39.581 | 0.9682 |
| 12 | 7274496 | 1559552 | 3312640 | 82.76 | 63.39 | 2.12 | 40.749 | 0.9902 | 38.518 | 0.9794 |
| Avg | | 1365845 | 2622464 | 84.90 | 71.02 | 1.92 | 41.89 | 0.99 | 39.37 | 0.97 |

Depth Information Storage

Figure 7:
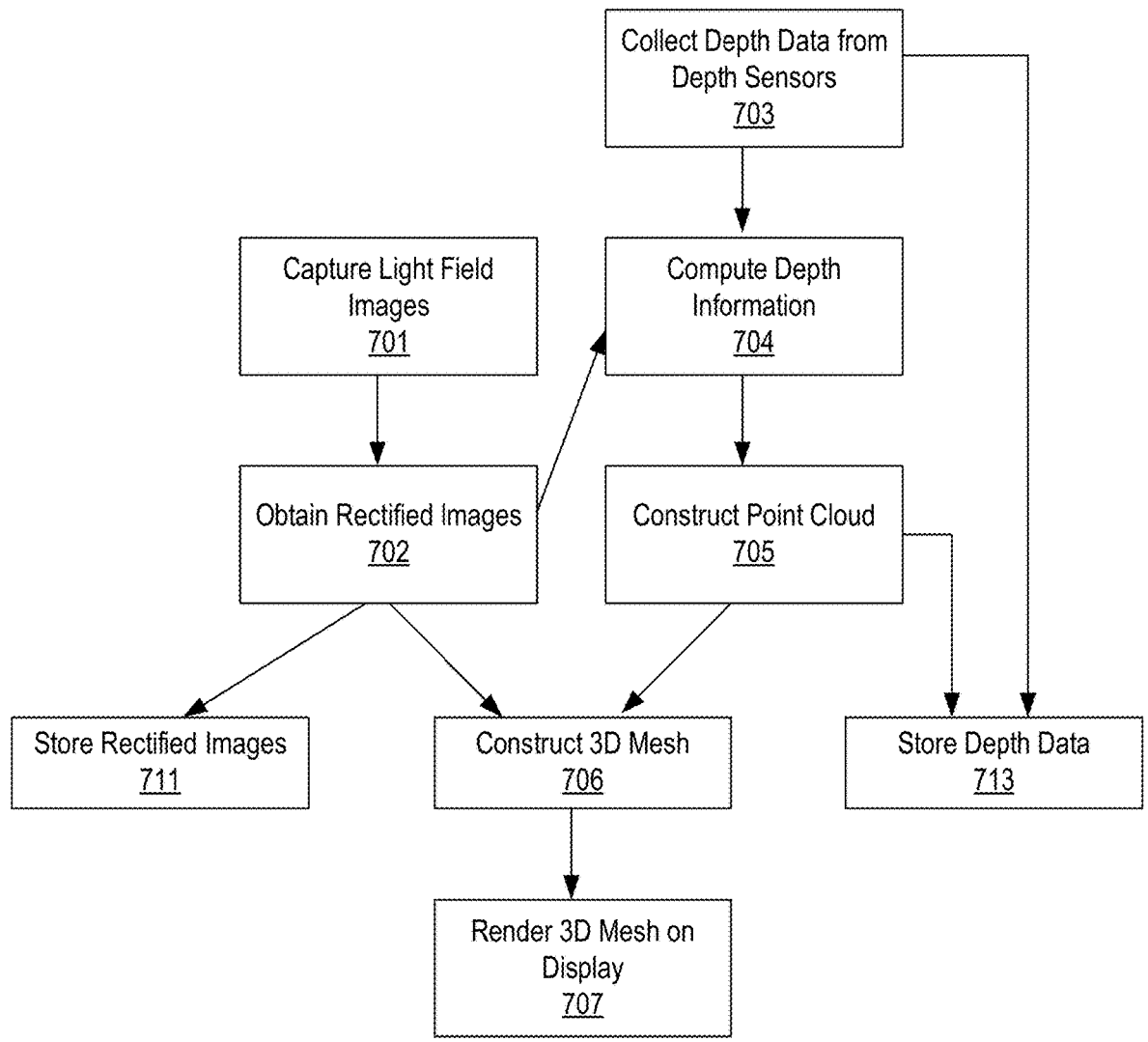
FIG. 7 illustrates a conventional processing flow of constructing a point cloud and a Three-Dimensional (3D) mesh.

When the camera array includes light field cameras, the captured light field includes spatial and angular information of the light from a scene. The captured light field is typically recorded as a combination of images and a point cloud. Point cloud data is a collection of 3D points, each having three floating-point coordinates designating a location in space. FIG. 7 illustrates a conventional processing flow of constructing the point cloud and the 3D mesh. As shown in FIG. 7, in operation 701, the light field images are captured by the camera array. The captured images are rectified at operation 702 and stored to disk at operation 711.

The rectified images can be used to compute depth information at operation 704. The computation of the depth information can also be based on the depth data from the depth sensors collected at operation 703. At operation 705, a point cloud is constructed using the computed depth information. At operation 706, the point cloud and the rectified images are used to construct the 3D mesh, which is then rendered and displayed at operation 707 (e.g., during the medical procedure).

Different mechanisms have been adopted to store the depth information obtained in the process shown in FIG. 7. One option is to store the point cloud data in a compressed format at operation 713. Alternatively, or in addition, compressed data collected from the depth sensor (together with calibration metadata attached) can be stored at operation 713. Storing the depth data from the depth sensors separately can yield a small data footprint. However, for each playback of the recorded scene, the stored rectified images and the stored depth data need to be re-processed to re-construct the point cloud and the 3D mesh. This wastes computational resources that could be used in other more important processes to render the volumetric data. On the other hand, storing the complete point cloud (in compressed form) or the 3D mesh increases the data footprint, especially for medical procedures that last many hours.

Figure 8:
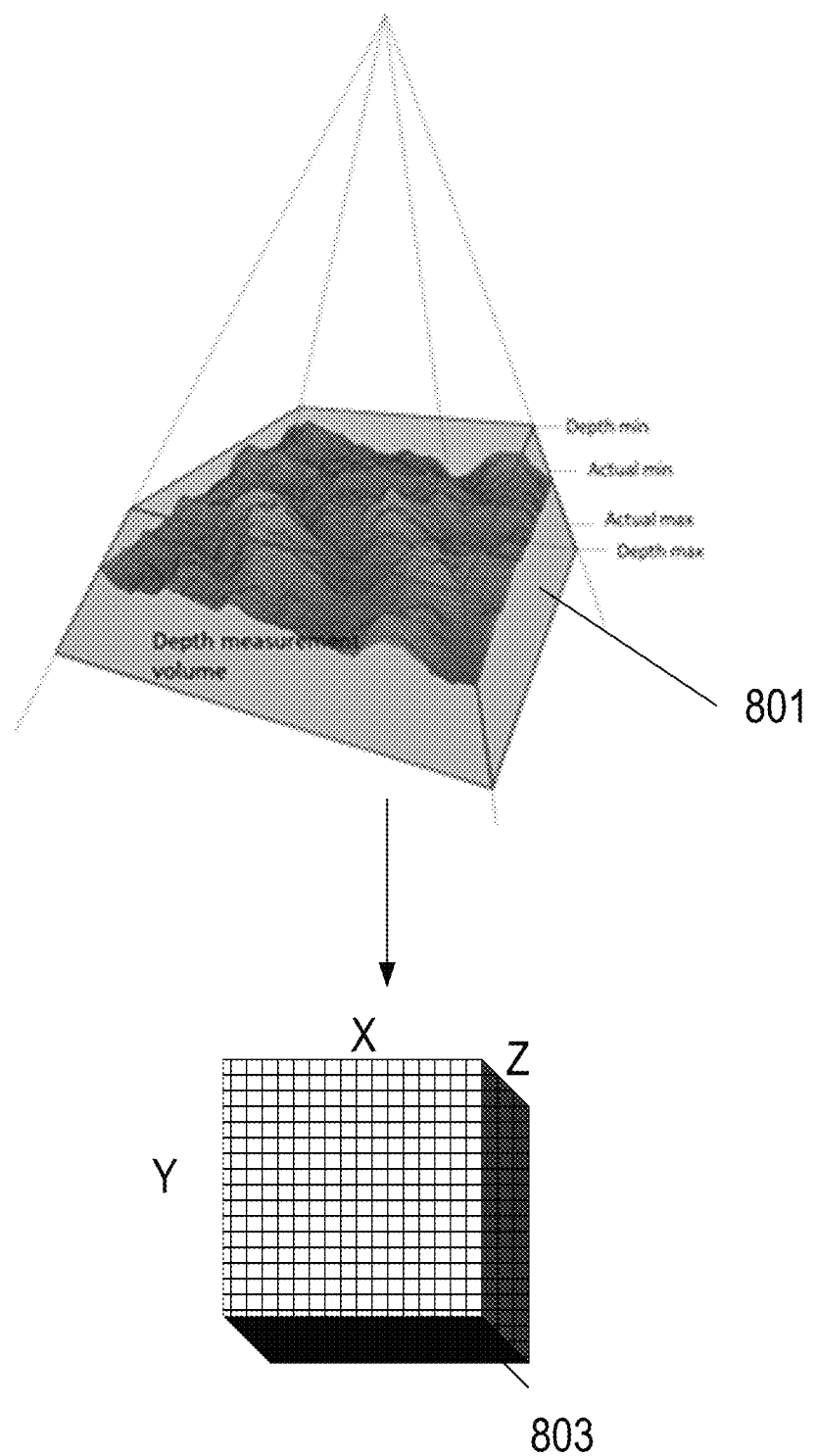
FIG. 8 illustrates an example depth measurement volume in accordance with embodiments of the present technology.

FIG. 8 illustrates an example depth measurement volume in accordance with embodiments of the present technology that overcomes these shortcomings. First, given the optical configuration of the imaging system 100 (e.g., the focal plane of the lenses in the camera array, the hardware configuration of the depth sensor, etc.), the minimum and maximum values of the detectable depth can be determined to provide a measurement volume that corresponds to a frustrum 801. The measurement volume can be quantized into 3D grids 803 according to the resolution requirements. After the quantization, points in the frustrum can be represented using integer values (e.g., 8-12 bits) instead of three floating-point coordinates (e.g., 16 or 32 bits each depending on precision), such as X units in width, Y units in length, and Z units in depth while X, Y and Z are non-negative integers. In particular, the positions along the X and Y axes can be represented inherently using the pixel coordinates. The position along the Z axis can be represented using a quantized value (e.g., N bits, N>1). The value of N is determined by the depth range (e.g., the maximum value of Z). In some embodiments, N is greater than or equal to $\lceil \log_2(Z) \rceil$. For example, if the system requires a granularity of 0.3 mm in width, height, and depth, a measurement volume having 45 cm in width, 45 cm in height, and 15 cm in depth can be quantized into an image with 1500×1500 pixels, each pixel having 500 depth levels that can be represented using 9 bits (N≥$\lceil \log_2(500) \rceil$).

In some embodiments, the quantization of the X and Y dimensions can be determined based on the resolution of the rectified images, so that the point data (stored in the format of an image) and the rectified images share the same resolution and can be packed together for storage and distribution. In some embodiments, the level(s) of quantization and the number of bits needed to represent Z values can be adjusted according to system requirements. For example, both a high-level and a low-level quantized point cloud can be generated, with one being used for display during the procedure (for better precision) and one being broadcasted over the network for playback (for faster transmission).

In some embodiments, a selective compression approach can be used to compress the point cloud represented in the image format. The depth bits can be divided into two portions and compressed differently using two different compression algorithms. For example, the most significant bits (e.g., 2 to 4 bits) representing the depth often include noise that have repetitive patterns. Therefore, techniques such as Run Length Encoding (RLE), which allows efficient data compression for information bits that are repeated consistently, can increase compression efficiency for the most significant bits. The remaining bits can be compressed using other types of compression techniques that are suitable for non-repetitive data.

Given a measurement volume determined by the optical configuration of the system, the disclosed techniques can be used to maintain the high degree of accuracy for depth data storage with a much smaller data footprint, eliminating the need to repeatedly process the captured depth data to re-create the 3D representation of the scene (e.g., for both real-time rendering and future playbacks).

Auxiliary Data Storage

Referring back to FIG. 1, auxiliary data, such as the positions and poses of the instruments 101 and trackers 113a-n, is also recorded during procedures to facilitate the display and replay of the recorded data. The pose of an instrument or a tracker includes translational and rotational positions at a particular moment in time. The imaging system 100 can support multiple types of instruments and trackers and be configured to record the poses with a sufficient time resolution. In some embodiments, the poses are captured with a time resolution that is consistent with the capability of the tracking hardware (e.g., 120 Hz or higher) to avoid latencies and thereby provide real-time or near real-time display and control of the instrument or tracker. For example, to provide real-time or near real-time feedback to surgeons so as to achieve accurate performance during the procedures, the system needs to achieve a latency of four milliseconds or less. However, once the surgical operation is complete, control of the instrument or tracker is no longer needed. Therefore, the recording of the poses for playback display can be performed at a lower time resolution (e.g., 60 Hz or lower), thereby reducing data footprint for storing auxiliary data.

In some embodiments, auxiliary data includes imaging data of other modalities, such as Computed Tomography (CT) scans and Magnetic Resonance Imaging (MRI) data, that can be overlayed or combined with the RGB and depth data captured by the system. That is, other types of imaging or volumetric data can be processed and correlated to the captured RGB and depth data (e.g., using image registration techniques) so that more information can be provided at a particular location of the scene to achieve a more accurate reconstruction of the medical procedure.

System Data Storage

Additional types of data, such as the system configurations, calibration parameters, system logs, or any changes of the hardware parameters, are also stored during the capture time. Some of these types of data are persistent (e.g., system configuration) and only needs to be stored/stream once. The non-persistent data (e.g., any changes in system or hard parameters) can be stored continuously or when a corresponding triggering event occurs. The storage of the system data ensures data completeness for future playbacks and/or auditing of the data for insurance or litigation uses.

Selected Embodiments of Data Integrity Assurance

Data integrity continues to be a persistent problem in the healthcare industry. Systems that maintain data integrity using static logs are still prone to change or modification when data is exported to external systems for analysis. Furthermore, the static logs can also be changed or altered through database or even manual updates given a sufficient access level. Instead of using the static logs, a patient ledger for surgical recordings can be implemented in the form of a blockchain to ensure data integrity of the entire medical procedure.

Figure 9A:
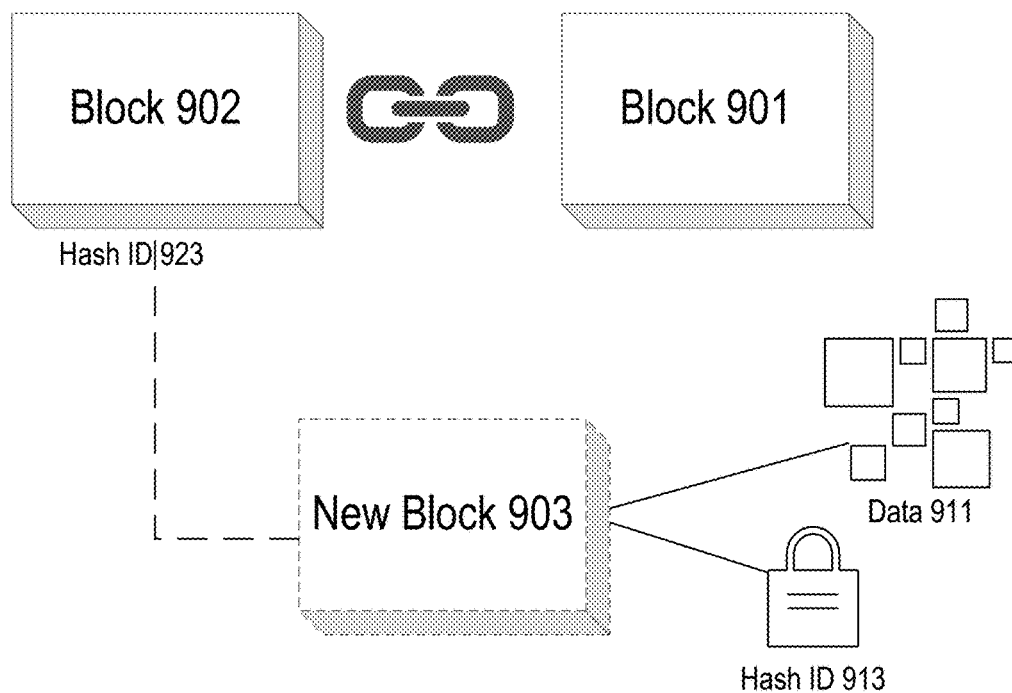
FIG. 9A illustrates an example procedure of generating a block for surgical data integrity in accordance with embodiments of the present technology.

FIG. 9A illustrates an example procedure of generating a block for surgical data integrity in accordance with embodiments of the present technology. To generate a new procedure event block 903, the transactional data of the event 911 becomes the input to a hash algorithm. The hash algorithm uses a series of attributes to form the hash identifier (ID) 913. In some embodiments, the hash ID 913 include a special token that represents a timestamp, a time-between-last-event (e.g., the time between this event and the previous event), an operator, an instrument, a location, and/or a type of event that has occurred. Examples of such events include a user inserting implants, setting trajectories of tools, recording video and audio, exporting media data, and other miscellaneous interaction with the primary user-interface. The hash algorithm creates a unique fingerprint that is associated to the event block 903. The event block is appended to the chain of blocks 901, 902 and references the unique fingerprint of the predecessor (e.g., hash ID 923 of Block 902), thereby ensuring that the order of events remains consistent across an entire medical procedure.

Figure 9B:
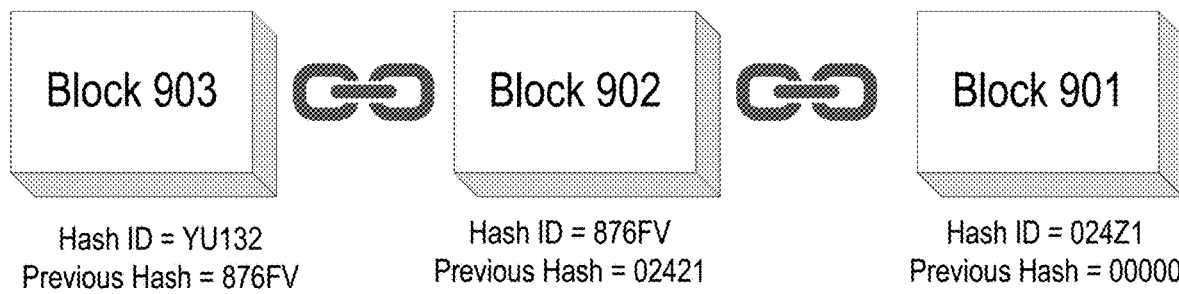
FIG. 9B illustrates an example chain of blocks for surgical data integrity in accordance with embodiments of the present technology.

FIG. 9B illustrates an example chain of blocks for surgical data integrity in accordance with embodiments of the present technology. In some embodiments, metadata can be included in the blocks of the ledger to provide a timeline to review events that occurred within the procedure (e.g., when being played alongside raw captured video). Data elements such as a unique timestamp of an event; event actions, a pre-shared key known by the apparatus for each unique system, and the user for whom generated the event are examples of what are used to create a secure checksum used to validate the unique block in the patient ledger.

Figure 9C:
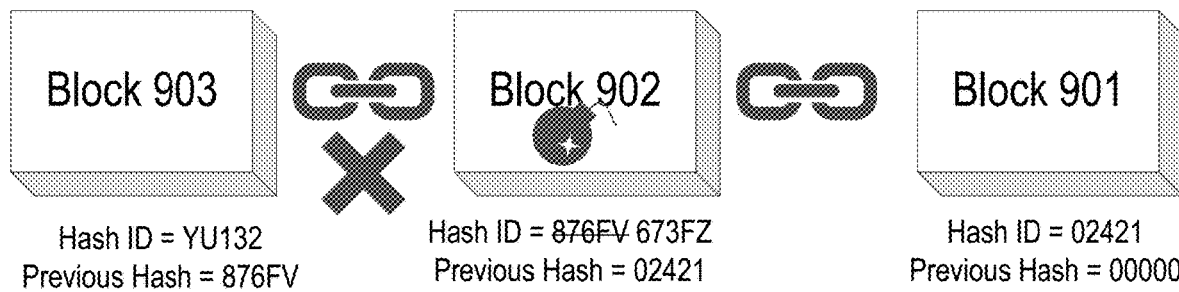
FIG. 9C illustrates an example of a proof-of-work failure indicating that the ledger has been modified in accordance with embodiments of the present technology.

Each event block within a procedure maintains its integrity by using the data within that event block to validate itself as part of the chain. Any modification of the data via the appropriate access level(s) can be detected through the proof-of-work checks. In block chain methodologies, a proof-of-work check refers to a mechanism to verify and validate that blocks within a chain have not been tampered with and that its integrity is maintained. The proof-of-work check provides comprehensive traceability of events that occur during the procedure as well as events that occur after the data is captured. For example, when the data is transferred or exported from one system to another, a proof-of-work check can be performed to determine whether data of the procedural events remain intact. Transferred procedural events that fail the proof-of-work check are audited and system administrators can be notified when the patient data within a procedural ledger has been modified. FIG. 9C illustrates an example of a proof-of-work failure indicating that the ledger has been modified in accordance with embodiments of the present technology. In this example, one of the event blocks (e.g., Block 902) has been tampered with. The modification of the block content results in a change in its hash value (e.g., from 876FV to 673FZ). Because a subsequent or a successor event block refers to the original hash value (e.g., 876FV) which is no longer a part of the chain, the proof-of-work check can detect such inconsistency and notify system administrators that the chain has broken (the integrity of the data has been tampered with). As another example, different uses of the data (e.g., analysis of the data, sharing the data for educational or research purposes with internal or external consumers) can be traced and verified using the proof-of-work check.

The proof-of-work also ensures the integrity and authenticity of the recorded data, especially during playback time to investigate a particular cause for a surgical complication or failure. Furthermore, if any part of the captured data needs to be removed (e.g., under legal requirements), such removal events can also be kept as part of the blockchain-based ledger to indicate when the removal was performed, for what reason(s), and/or through what mechanism(s). The use of the blockchain-based ledger can provide comprehensive traceability of events that occur during or after the procedure that cannot be achieved using the conventional static logs.

Selected Embodiments of Data Distribution

In some embodiments, the captured data can be first stored in local repositories (e.g., disk storages). The data can be optionally transmitted to remote servers after the capturing completes if needed. In some embodiments, to enable real-time display of the data (e.g., to the surgeon performing the procedure), the captured data is stored locally and streamed to remote repositories (e.g., files streams, disk storages) during the procedure to minimize latencies. Because the majority of the data is temporal in structure, distribution and replay of the captured data can be performed concurrently with the real-time display of such data. That is, part of the captured data can be distributed and replayed remotely during the procedure without the need for the entire dataset to be present.

Figure 10:
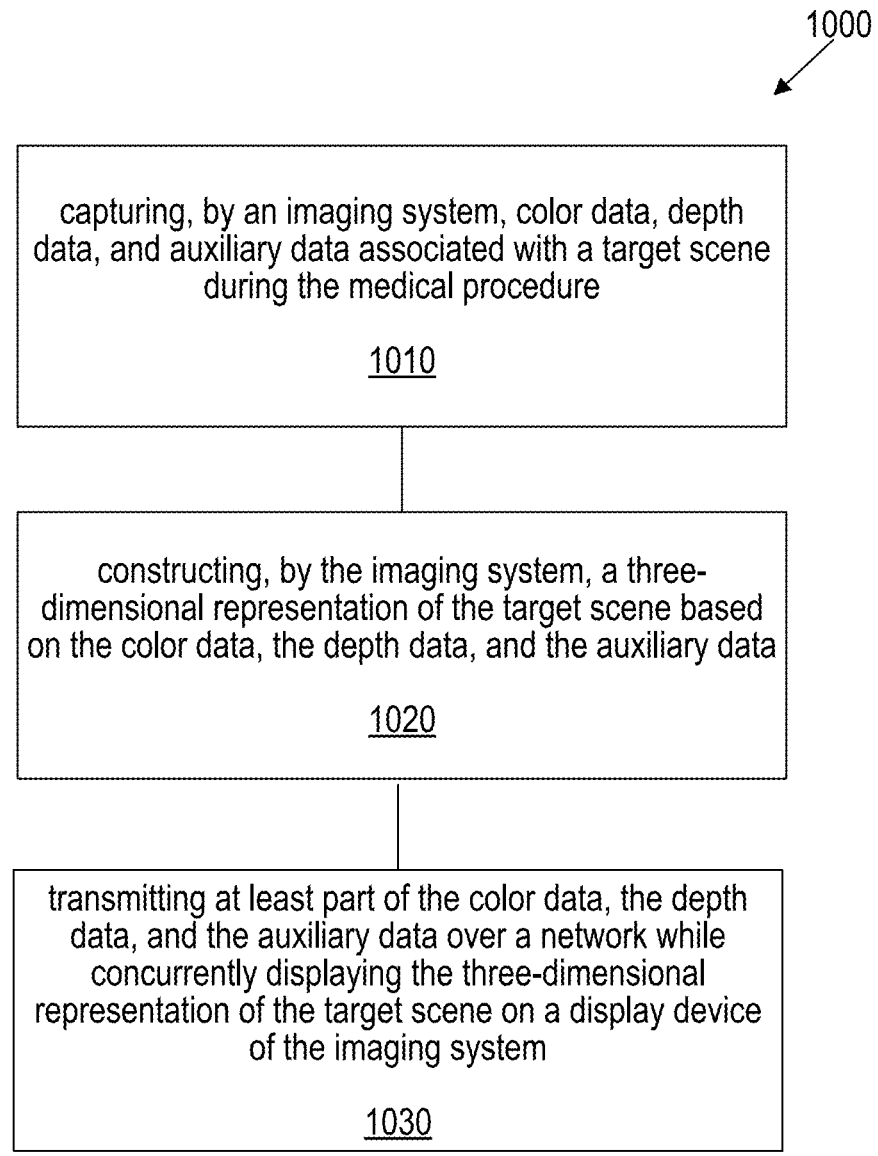
FIG. 10 is a flowchart representation of a method for displaying and distributing recorded data in accordance with embodiments of the present technology.

FIG. 10 is a flowchart representation of a method 1000 for displaying and distributing recorded data for a medical procedure in accordance with embodiments of the present technology. The method 1000 includes, at operation 1010, capturing, by an imaging system, color data, depth data, and auxiliary data associated with a target scene during the medical procedure. The method 1000 includes, at operation 1020, constructing, by the imaging system, a three-dimensional representation of the target scene based on the color data, the depth data, and the auxiliary data. The method 1000 includes, at operation 1030, transmitting at least part of the color data, the depth data, and the auxiliary data over a network. In some embodiments, the transmitting of the data can be performed after the capturing completes. In some embodiments, the transmitting of the data is performed while concurrently displaying the three-dimensional representation of the target scene on a display device of the imaging system.

To achieve the concurrent distribution and replay of the captured data, the data can be divided into multiple chunks or units each having a predetermined size that is suitable for network transmissions. Each chunk or unit can include corresponding metadata to ensure cohesiveness between the locally stored data and the distributed/transmitted copy. Whether data be stored locally or transmitted remotely for analysis, each segment of data interlocks, or links, to its predecessor through a unique checksum to ensure that segments can be referenced in order. This interlocking of data segments ensures that data integrity can be achieved when data is lost in transmission (e.g., due to disconnect or interruption). The entirety of data transmitted comes with a unique checksum itself. The checksum can be encrypted (e.g., using one-way-hash SHA256 encryption). Once the data is retrieved, the receiving system can validate the unique checksum for the entirety of data received by the apparatus, ensuring all data was transmitted successfully. The disclosed techniques can enable remote streaming or broadcasting of the medical procedure so as to allow remote expert consultation of an on-going procedure.

Example Playback and Editing

Figure 11A:
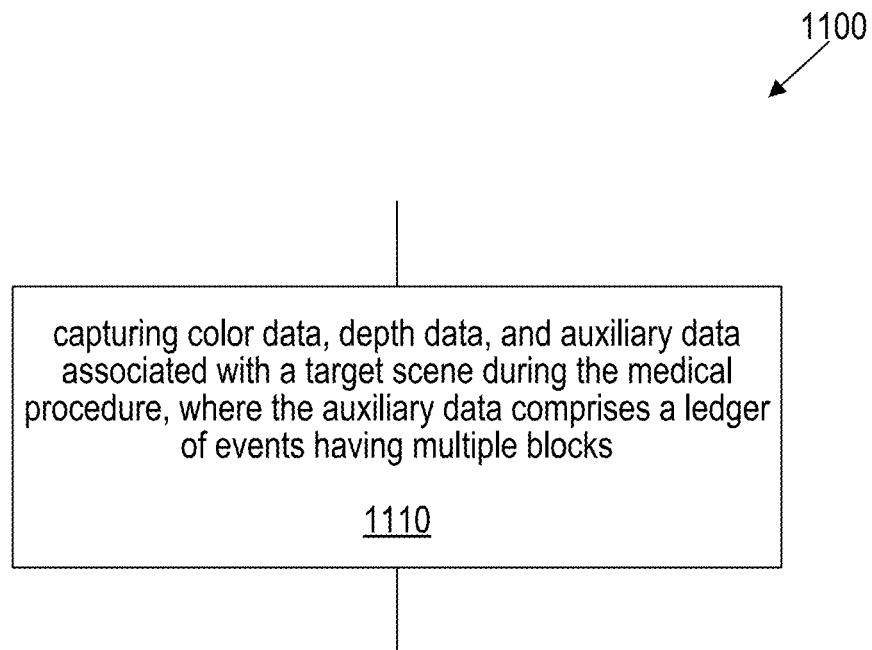
FIG. 11A is a flowchart representation of a method for capturing data in accordance with embodiments of the present technology.

FIG. 11A is a flowchart representation of a method 1100 for capturing a medical procedure in accordance with embodiments of the present technology. The method 1100 includes, at operation 1110, capturing color data, depth data, and auxiliary data associated with a target scene during the medical procedure. The auxiliary data comprises a ledger of events having multiple blocks. Each of the multiple blocks represents an event that has occurred during the medical procedure and is associated with a unique identifier generated using data in a block and at least a timestamp associated with the event. In some embodiments, the method also includes storing a three-dimensional representation of the target scene based on the color data, the depth data, and the auxiliary data.

Figure 11B:
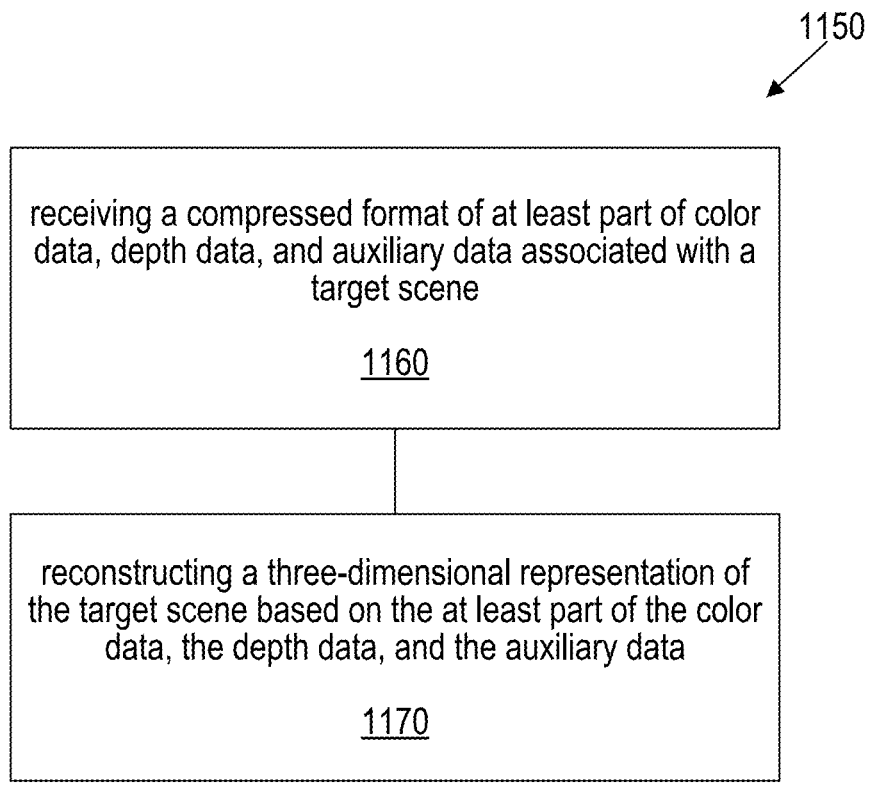
FIG. 11B is a flowchart representation of a method for replaying a recorded medical procedure in accordance with embodiments of the present technology.

Once the captured data is distributed across the network, the data can be played back and/or edited for a variety of reasons. FIG. 11B is a flowchart representation of a method 1150 for replaying a recorded medical procedure in accordance with embodiments of the present technology. The method 1150 includes, at operation 1160, receiving a compressed format of at least part of color data, depth data, and auxiliary data associated with a target scene. The color data, depth data, and the auxiliary data are captured during the medical procedure. In some embodiments, the auxiliary data comprises a ledger of events having multiple blocks. Each of the blocks represents an event that has occurred during the medical procedure and is associated with a unique identifier generated using data in the block and at least a timestamp associated with the event. The method 1150 also includes, at operation 1170, reconstructing a three-dimensional representation of the target scene based on the at least part of the color data, the depth data, and the auxiliary data. In some embodiments, the method includes displaying the three-dimensional representation of the target scene from a perspective that was not visible or available during the medical procedure.

In some embodiments, personal information of the patients is removed during the capturing process so that the information is never recorded or shared. In some embodiments, the recordings can be edited to remove personal information of the patients after the recording completes such that the recordings can be shared among surgeons and/or medical students for educational purposes. Such edits to the recordings can be reflected in the audit logs and/or administrator notifications during the proof-of-work check to clearly demonstrate the information that has been removed/revised. Data elements considered education or de-identified can be anonymized before being entered into the patient's ledger or re-generated through post processing events. Such techniques need to maintain data integrity of the ledger itself as any modification to such ledger can invalidate the authenticity of the original ledger. Elements captured from within the ledger can be used by machine learning to generate models related to "time-on-task" (the amount of time a surgeon spends on a particular event) for procedures, implant accuracy, trajectory paths, and surgical automation.

In some embodiments, the playback of the recorded data can be used to assess surgical performance. The surgeons can review the recordings of the procedures that they have performed to identify areas that need further improvements. In particular, the reconstructed scene can be viewed from different perspectives of the scene that were not available during the procedure.

In some embodiments, the recordings can assist the evaluation of medical insurance claims or medical litigation claims. For example, the care provider can review the recordings to determine whether a particular claim has valid grounds based on the events that occurred during the procedure. Alternatively, or in addition, the payer can review the recordings to contest whether the particular claim has valid grounds. The different perspectives offered by the reconstructed scene can provide additional information that may not be recalled by the surgeon. As another example, when portions of the data are removed (e.g., to comply with certain legal requirements or under discretions of the users), the blockchain-based ledger ensures that information about the removal event(s) is accurately captured. Reasons for the removal and/or mechanisms with which the removal was performed can be stored as part of the chain in the ledger. Such comprehensive traceability of the events can provide robust protections to consumers and/or care providers.

Figure 12:
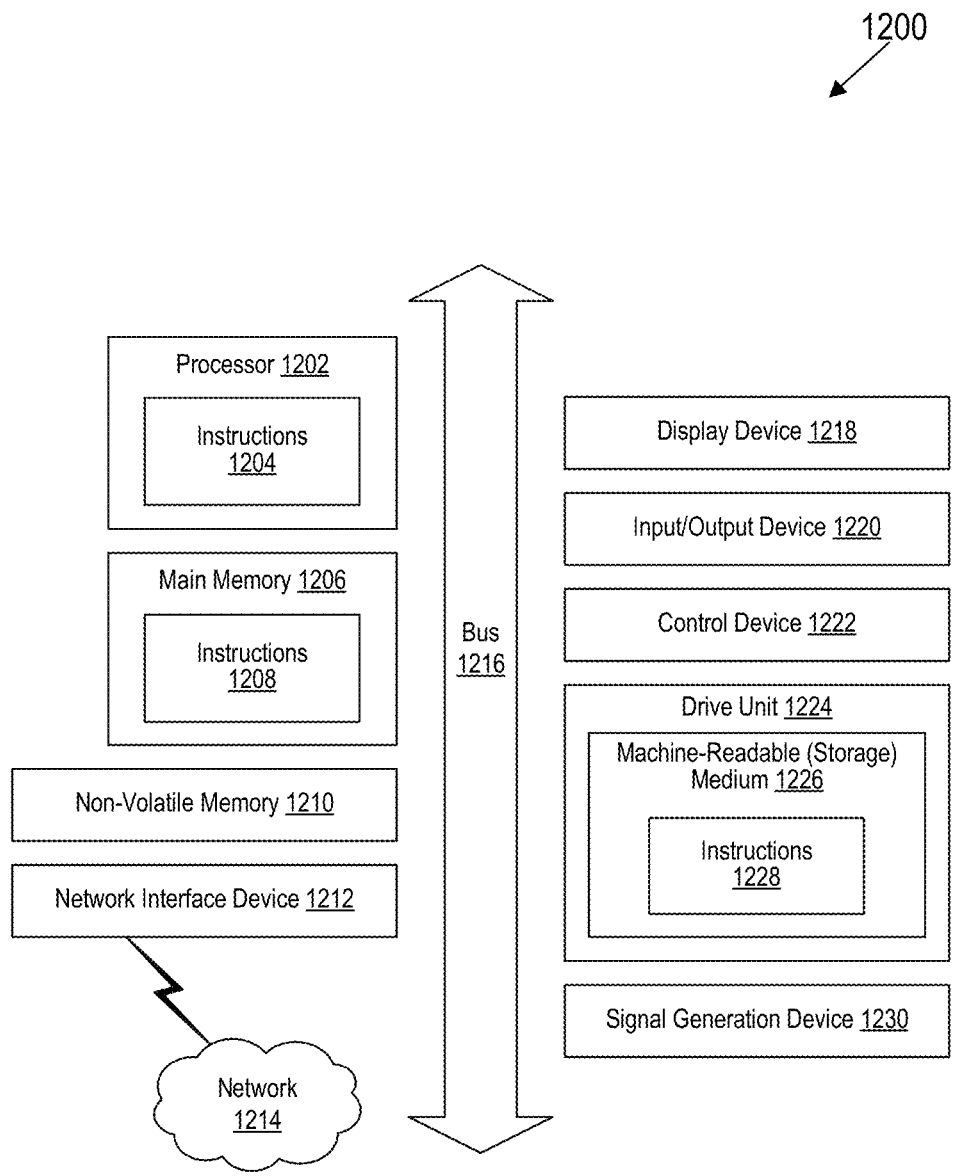
FIG. 12 is a block diagram that illustrates an example of a computer system in which at least some operations described herein can be implemented.

FIG. 12 is a block diagram that illustrates an example of a computer system 1200 in which at least some operations described herein can be implemented. As shown, the computer system 1200 can include: one or more processors 1202, main memory 1206, non-volatile memory 1210, a network interface device 1212, video display device 1218, an input/output device 1220, a control device 1222 (e.g., keyboard and pointing device), a drive unit 1224 that includes a storage medium 1226, and a signal generation device 1230 that are communicatively connected to a bus 1216. The bus 1216 represents one or more physical buses and/or point-to-point connections that are connected by appropriate bridges, adapters, or controllers. Various common components (e.g., cache memory) are omitted from FIG. 7 for brevity. Instead, the computer system 1200 is intended to illustrate a hardware device on which components illustrated or described relative to the examples of the figures and any other components described in this specification can be implemented.

The computer system 1200 can take any suitable physical form. For example, the computing system 1200 can share a similar architecture as that of a server computer, personal computer (PC), tablet computer, mobile telephone, game console, music player, wearable electronic device, network-connected ("smart") device (e.g., a television or home assistant device), AR/VR systems (e.g., head-mounted display), or any electronic device capable of executing a set of instructions that specify action(s) to be taken by the computing system 1200. In some implementation, the computer system 1200 can be an embedded computer system, a system-on-chip (SOC), a single-board computer system (SBC) or a distributed system such as a mesh of computer systems or include one or more cloud components in one or more networks. Where appropriate, one or more computer systems 1200 can perform operations in real-time, near real-time, or in batch mode.

The network interface device 1212 enables the computing system 1200 to mediate data in a network 1214 with an entity that is external to the computing system 1200 through any communication protocol supported by the computing system 1200 and the external entity. Examples of the network interface device 1212 include a network adaptor card, a wireless network interface card, a router, an access point, a wireless router, a switch, a multilayer switch, a protocol converter, a gateway, a bridge, bridge router, a hub, a digital media receiver, and/or a repeater, as well as all wireless elements noted herein.

The memory (e.g., main memory 1206, non-volatile memory 1210, machine-readable medium 1226) can be local, remote, or distributed. Although shown as a single medium, the machine-readable medium 1226 can include multiple media (e.g., a centralized/distributed database and/or associated caches and servers) that store one or more sets of instructions 1228. The machine-readable (storage) medium 1226 can include any medium that is capable of storing, encoding, or carrying a set of instructions for execution by the computing system 1200. The machine-readable medium 1226 can be non-transitory or comprise a non-transitory device. In this context, a non-transitory storage medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-readable media include recordable-type media such as volatile and non-volatile memory devices 1210, removable flash memory, hard disk drives, optical disks, and transmission-type media such as digital and analog communication links.

In general, the routines executed to implement examples herein can be implemented as part of an operating system or a specific application, component, program, object, module, or sequence of instructions (collectively referred to as "computer programs"). The computer programs typically comprise one or more instructions (e.g., instructions 1204, 1208, 1228) set at various times in various memory and storage devices in computing device(s). When read and executed by the processor 1202, the instruction(s) cause the computing system 1200 to perform operations to execute elements involving the various aspects of the disclosure.

ADDITIONAL EXAMPLES

The following examples are illustrative of several embodiments of the present technology:

1. An imaging system, comprising:
   a camera array configured to capture multiple images of a scene, wherein each of the multiple images includes color data represented in a Bayer pattern that includes a blue channel, two green channels, and a red channel; and
   an image processing device configured to:
      receive the multiple images captured by the camera array,
      split each of the multiple images represented in the Bayer pattern into four individual color planes,
      form at least one set of data by combining the four individual color planes of the multiple images, and
      compress the at least one set of data.

2. The imaging system of example 1, wherein the at least one set of data is formed by stacking the four individual color planes of each of the multiple images.

3. The imaging system of example 1 or example 2, wherein the multiple images include a first frame captured by a camera in the camera array at a first time in time domain and a second frame captured by the camera at a second time in time domain,
   wherein the image processing device is configured to form at least three sets of data by:
      forming a first set of data by combining the blue channel of the first frame with the blue channel of the second frame;
      forming a second set of data by combining the red channel of the first frame with the red channel of the second frame; and
      forming at least a third set of data by combining the two green channels of the first frame with the two green channels of the second frame.

4. The imaging system of example 3, wherein the image processing device is configured to compress the at least one set of data using at least a motion detection compression technique.

5. The imaging system of any one of examples 1 to 4, wherein the camera array includes a first camera and a second camera, the first camera configured to capture a first frame of the scene at a first time in a time domain from a first angle, the second camera configured to capture a second frame of the scene at the same first time in the time domain from a second angle, wherein the image processing device is configured to form at least three sets of data by:
  forming a first set of data by combining the blue channel of the first frame with the blue channel of the second frame;
  forming a second set of data by combining the red channel of the first frame with the red channel of the second frame; and
  forming at least a third set of data by combining the two green channels of the first frame with the two green channels of the second frame.

6. The imaging system of any one of examples 1 to 5, wherein the image processing device is configured to:
  generate a point cloud dataset of the scene based on depth information of the scene;
  quantize the point cloud dataset into a three-dimensional volume having X units in width, Y units in length, and Z units in depth, X, Y, and Z being non-negative integers; and
  store the point cloud dataset in an image data format having a width of X and a height of Y, and wherein each pixel of the image data format is represented using N bits, N being greater than or equal to $\lceil \log_2(Z) \rceil$.

7 The imaging system of example 6, wherein the image processing device is configured to:
  compress a most significant M bits of the N bits using a first compression technique; and
  compress remaining (N-M) bits using a second compression technique that is different than the first compression technique.

8. The imaging system of example 6, wherein the camera array includes one or more light field cameras configured to capture a light field of the scene that comprises the depth information of the scene.

9. The imaging system of example 6, further comprising a depth sensor configured to detect the depth information of the scene.

10. The imaging system of any one of examples 1 to 9, further comprising an integrity processing device configured to:
  generate a unique identifier of a first block representing an event that has occurred during capturing of the scene, wherein the unique identifier of the first block is based on data in the first block and at least a timestamp associated with the event.

11. The imaging system of example 10, wherein the integrity processing device is further configured to:
  form a ledger of events by appending the first block to one or more previously generated blocks.

12. A method for displaying and distributing recorded data, comprising:
  capturing, by an imaging system, color data, depth data, and auxiliary data associated with a target scene;
  compressing the color data, the depth data, and the auxiliary data; and
  constructing, by the imaging system, a three-dimensional representation of the target scene based on the color data, the depth data, and the auxiliary data.

13. The method of example 12, further comprising:
  transmitting at least part of the color data, the depth data, and the auxiliary data over a network.

14. The method of example 13, wherein the transmitting is performed concurrently with displaying the three-dimensional representation of the target scene on a display device of the imaging system.

15. The method of any one of examples 12 to 14, wherein compressing the color data comprises:
  capturing the color data of the target scene represented in a Bayer pattern, wherein the Bayer pattern includes a blue channel, two green channels, and a red channel;
  splitting each of the color data represented in the Bayer pattern into four individual color planes;
  forming at least one set of data by combining the four individual color planes; and
  compressing the at least one set of data using one or more compression techniques.

16. The method of example 15, wherein the at least one set of data is formed by stacking the four individual color planes.

17. The method of example 15, wherein the at least one set of data is formed based on a temporal or spatial coherency of the color data.

18. The method of example 15, wherein compressing the depth data comprises:
  capturing depth information of the target scene using a camera array or a depth sensor;
  generating a point cloud dataset of the target scene based on the depth information;
  storing the point cloud dataset in an image data format having a width of X and a height of Y, and wherein each pixel of the image data format is represented using Z bits, X, Y, and Z being positive integers;
  compressing a most significant M bits of the Z bits using a first compression technique; and
  compressing remaining (Z-M) bits using a second compression technique that is different than the first compression technique.

19. The method of any one of examples 12 to 18, wherein the auxiliary data comprises translational or rotational information collected by one or more tracking devices, and wherein compressing the auxiliary data comprises:
  recording the translational or rotational information of the one or more tracking devices at a predefined frequency that is lower than a capability of the one or more tracking devices.

20. The method of any one of examples 12 to 19, further comprising:
  dividing the color data, the depth data, and the auxiliary data into multiple chunks each having a predetermined size; and
  transmitting one or more of the multiple chunks of the color data, the depth data, and the auxiliary data over a network.

21. A non-transitory computer program medium having code stored thereon, the code, when executed by one or more processors, causing the one or more processors to:
  capture color data, depth data, and auxiliary data associated with a target scene;
  compress the color data, the depth data, and the auxiliary data, wherein the color data of the target scene represented in a Bayer pattern, wherein the Bayer pattern includes a blue channel, two green channels, and a red channel, and wherein the depth data comprises a point cloud dataset of the target scene; and
  construct a three-dimensional representation of the target scene based on the color data, the depth data, and the auxiliary data.

22. The non-transitory computer program medium of example 21, wherein the one or more processors are configured to:
split the color data represented in the Bayer pattern into four individual color planes; form at least one set of data by combining the four individual color planes; and compress the at least one set of data using one or more compression techniques.
23. The non-transitory computer program medium of example 22, wherein the one or more processors are configured to form at least one set of data by stacking the four individual color planes.
24. The non-transitory computer program medium of any one of examples 21 to 23, wherein the one or more processors are configured to form at least one set of data based on a temporal or spatial coherency of the color data.
25. The non-transitory computer program medium of any one of examples 21 to 24, wherein the one or more processors are configured to:
quantize the point cloud dataset into a three-dimensional volume having X units in width, Y units in length, and Z units in depth, X, Y, and Z being non-negative integers; and
store the point cloud dataset in an image data format having a width of X and a height of Y, and wherein each pixel of the image data format is represented using N bits, N being greater than or equal to $\lceil \log_2(Z) \rceil$.
26. The non-transitory computer program medium of example 25, wherein the one or more processors are configured to:
compress a most significant M bits of the N bits using a first compression technique; and
compress remaining (N-M) bits using a second compression technique that is different than the first compression technique.
27. The non-transitory computer program medium of any one of examples 21 to 26, wherein the auxiliary data comprises translational or rotational information collected by one or more tracking devices, and wherein the one or more processors are configured to:
record the translational or rotational information of the one or more tracking devices at a predefined frequency that is lower than a capability of the one or more tracking devices.
28. The non-transitory computer program medium of any one of examples 21 to 27, wherein the one or more processors are configured to:
transmit at least part of the color data, the depth data, and the auxiliary data over a network concurrently with displaying the three-dimensional representation of the target scene on a display device.
29. A method for generating a ledger for data captured during a medical procedure, comprising:
determining an event associated with the medical procedure;
generating an event block using data associated with the event, wherein the event block is associated with a unique identifier generated based on data of the event; and
appending the event block to a chain of blocks representing events that have occurred in the medical procedure.
30. The method of example 29, wherein the unique identifier comprises a hash identifier generated by inputting the data of the event into a hash algorithm.
31. The method of example 29 or example 30, wherein the event associated with the medical procedure comprises at least one of: inserting an implant, setting a trajectory of a tool, recording a video or an audio of the medical procedure, or exporting media data associated with the medical procedure.
32. The method of any one of examples 29 to 31, wherein the unique identifier comprises a token that represents at least one of a timestamp, a time between the event and a previous event, an operator, an instrument, a location, or a type of event that has occurred.
33. The method of any one of examples 29 to 32, wherein the chain of blocks comprises metadata that indicate a timeline of the events that have occurred in the medical procedure.
34. The method of any one of examples 29 to 33, comprising:
validating that the event block is part of the chain of blocks using the data associated with the event.
35. The method of example 34, wherein the validating comprises:
determining a successor block of the event block in the chain of blocks;
determining a reference identifier referenced by the successor block; and
determining whether the event block is a valid block of the chain by comparing the unique identifier of the event block to the reference identifier.
36. The method of any one of examples 29 to 35, comprising:
encrypting a unique value associated with the chain of blocks; and
transmitting the chain of blocks over a network with the unique value.
37. The method of example 37, wherein the unique value comprises a checksum value of the chain of blocks.
38. A method for replaying a medical procedure, comprising:
receiving a compressed format of at least part of color data, depth data, and auxiliary data associated with a target scene, wherein the color data, depth data, and the auxiliary data are captured during the medical procedure, wherein the auxiliary data comprises a ledger of events having multiple blocks, wherein each of the multiple blocks represents an event that has occurred during the medical procedure; and
reconstructing a three-dimensional representation of the target scene based on the at least part of the color data, the depth data, and the auxiliary data.
39. The method of example 38, further comprising:
validating the ledger of the events using an encrypted unique value associated with the ledger of the events.
40. The method of example 38 or example 39, further comprising:
displaying the three-dimensional representation of part of the target scene that was not visible or available during the medical procedure.
41. The method of any one of examples 38 to 40, wherein each of the multiple blocks is associated with a unique identifier generated using data in the block and at least a timestamp associated with the event.
42. The method of any one of examples 38 to 41, further comprising:
validating that a first block is part of the ledger of events using data associated with the first block.

43. The method of example 42, wherein the validating comprises:
   determining a successor block of the first block in the ledger of events;
   determining a reference identifier referenced by the successor block; and
   determining whether the first block is a valid block by comparing a unique identifier of the first block to the reference identifier.
44. An integrity processing device for ensuring integrity of data captured during a medical procedure, comprising:
   a processor that is configured to:
   determine an event associated with the medical procedure;
   generate an event block using data associated with the event, wherein the event block is associated with a unique identifier generated based on data of the event; and
   append the event block to a chain of blocks representing events that have occurred in the medical procedure.
45. The integrity processing device of example 44, wherein the unique identifier comprises a hash identifier generated by inputting the data of the event into a hash algorithm.
46. The integrity processing device of example 44 or 45, wherein the event associated with the medical procedure comprises at least one of: inserting an implant, setting a trajectory of a tool, recording a video or an audio of the medical procedure, or exporting media data associated with the medical procedure.
47. The integrity processing device of any one of examples 44 to 46, wherein the unique identifier comprises a token that represents at least one of a timestamp, a time between the event and a previous event, an operator, an instrument, a location, or a type of event that has occurred.
48. The integrity processing device of any one of examples 44 to 47, wherein the chain of blocks comprises metadata that indicate a timeline of the events that have occurred in the medical procedure.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A method for displaying and distributing recorded data, comprising:
   capturing, by an imaging system, color data, depth data, and auxiliary data associated with a target scene, wherein the color data is represented in a Bayer pattern, and wherein the Bayer pattern includes a blue channel, two green channels, and a red channel;
   compressing the color data, the depth data, and the auxiliary data, wherein compressing the color data comprises:
      splitting each of the color data represented in the Bayer pattern into four individual color planes;
      forming at least one set of data by combining the four individual color planes; and
      compressing the at least one set of data using one or more compression techniques; and
   constructing, by the imaging system, a three-dimensional representation of the target scene based on the color data, the depth data, and the auxiliary data.
2. The method of claim 1, further comprising:
   transmitting at least part of the color data, the depth data, and the auxiliary data over a network.
3. The method of claim 2, wherein the transmitting is performed concurrently with displaying the three-dimensional representation of the target scene on a display device of the imaging system.
4. The method of claim 1, wherein the at least one set of data is formed by stacking the four individual color planes.
5. The method of claim 1, wherein the at least one set of data is formed based on a temporal or spatial coherency of the color data.
6. The method of claim 1, wherein compressing the depth data comprises:
   capturing depth information of the target scene using a camera array or a depth sensor;
   generating a point cloud dataset of the target scene based on the depth information;
   storing the point cloud dataset in an image data format having a width of X and a height of Y, and wherein each pixel of the image data format is represented using Z bits, X, Y, and Z being positive integers;
   compressing a most significant M bits of the Z bits using a first compression technique; and
   compressing remaining (Z-M) bits using a second compression technique that is different than the first compression technique.

7. The method of claim 1, wherein the auxiliary data comprises translational or rotational information collected by one or more tracking devices, and wherein compressing the auxiliary data comprises:
recording the translational or rotational information of the one or more tracking devices at a predefined frequency that is lower than a capability of the one or more tracking devices.

8. The method of claim 1, further comprising:
dividing the color data, the depth data, and the auxiliary data into multiple chunks each having a predetermined size; and
transmitting one or more of the multiple chunks of the color data, the depth data, and the auxiliary data over a network.

9. A non-transitory computer program medium having code stored thereon, the code, when executed by one or more processors, causing the one or more processors to:
capture color data, depth data, and auxiliary data associated with a target scene, wherein the color data of the target scene represented in a Bayer pattern, wherein the Bayer pattern includes a blue channel, two green channels, and a red channel, and wherein the depth data comprises a point cloud dataset of the target scene;
compress the color data, the depth data, and the auxiliary data, wherein compressing the color data comprises:
splitting the color data represented in the Bayer pattern into four individual color planes;
forming at least one set of data by combining the four individual color planes; and
compressing the at least one set of data using one or more compression techniques; and
construct a three-dimensional representation of the target scene based on the color data, the depth data, and the auxiliary data.

10. The non-transitory computer program medium of claim 9, wherein the one or more processors are configured to form at least one set of data by stacking the four individual color planes.

11. The non-transitory computer program medium of claim 9, wherein the one or more processors are configured to form at least one set of data based on a temporal or spatial coherency of the color data.

12. The non-transitory computer program medium of claim 9, wherein the auxiliary data comprises translational or rotational information collected by one or more tracking devices, and wherein the one or more processors are configured to:
record the translational or rotational information of the one or more tracking devices at a predefined frequency that is lower than a capability of the one or more tracking devices.

13. The non-transitory computer program medium of claim 9, wherein the one or more processors are configured to:
transmit at least part of the color data, the depth data, and the auxiliary data over a network concurrently with displaying the three-dimensional representation of the target scene on a display device.

14. A non-transitory computer program medium of having code stored thereon, the code, when executed by the one or more processors, causing the one or more processors to:
capture color data, depth data, and auxiliary data associated with a target scene, wherein the color data of the target scene represented in a Bayer pattern, wherein the Bayer pattern includes a blue channel, two green channels, and a red channel, and wherein the depth data comprises a point cloud dataset of the target scene;
quantize the point cloud dataset into a three-dimensional volume having X units in width, Y units in length, and Z units in depth, X, Y, and Z being non-negative integers; and
store the point cloud dataset in an image data format having a width of X and a height of Y, and wherein each pixel of the image data format is represented using N bits, N being greater than or equal to $\lceil \log_2(Z) \rceil$
compress the color data, the depth data, and the auxiliary data; and
construct a three-dimensional representation of the target scene based on the color data, the depth data, and the auxiliary data.

15. The non-transitory computer program medium of claim 14, wherein the one or more processors are configured to:
compress a most significant M bits of the N bits using a first compression technique; and
compress remaining (N-M) bits using a second compression technique that is different than the first compression technique.

16. A method for displaying and distributing recorded data, comprising:
capturing color data, depth data, and auxiliary data associated with a target scene, wherein the color data is represented in a Bayer pattern, and wherein the Bayer pattern includes a blue channel, two green channels, and a red channel;
compressing the color data, the depth data, and the auxiliary data, wherein compressing the color data comprises:
splitting each of the color data represented in the Bayer pattern into four individual color planes;
forming at least one set of data by combining the four individual color planes; and
compressing the at least one set of data using one or more compression techniques; and
constructing a three-dimensional representation of the target scene based on the color data, the depth data, and the auxiliary data.

* * * * *